United States Patent
Lait

(10) Patent No.: US 11,040,066 B2
(45) Date of Patent: Jun. 22, 2021

(54) TOPICAL COMPOSITION FOR USE IN THE TREATMENT OF BURNS

(71) Applicant: Safeguard Medical Holdco, LLC, Harrisburg, NC (US)

(72) Inventor: Mark Lait, Hertford (GB)

(73) Assignee: Safeguard Medical Holdco, LLC, Harrisburg, NC (US)

( * ) Notice: Subject to any disclaimer, the term of this patent is extended or adjusted under 35 U.S.C. 154(b) by 0 days.

(21) Appl. No.: 16/850,136

(22) Filed: Apr. 16, 2020

(65) Prior Publication Data

US 2020/0237816 A1 Jul. 30, 2020

Related U.S. Application Data

(63) Continuation of application No. PCT/IB2018/058089, filed on Oct. 18, 2018.

(30) Foreign Application Priority Data

Oct. 20, 2017 (GB) ..................... 1717224
Aug. 17, 2018 (GB) ..................... 1813442

(51) Int. Cl.
*A61K 35/08* (2015.01)
*A61P 17/02* (2006.01)
*A61K 9/00* (2006.01)
*A61K 9/70* (2006.01)
*A61K 47/10* (2017.01)
*A61K 47/34* (2017.01)

(52) U.S. Cl.
CPC ............ *A61K 35/08* (2013.01); *A61K 9/0014* (2013.01); *A61K 9/7007* (2013.01); *A61K 47/10* (2013.01); *A61K 47/34* (2013.01); *A61P 17/02* (2018.01)

(58) Field of Classification Search
CPC .............. A61K 47/10; A61K 2800/524; A61K 8/8182; A61K 47/02; A61K 8/43
See application file for complete search history.

(56) References Cited

U.S. PATENT DOCUMENTS

| 5,384,125 | A | 1/1995 | Dipippo et al. |
| 5,670,169 | A * | 9/1997 | Cornell ............... A61K 9/0014 |
| | | | 424/488 |
| 2014/0212513 | A1 | 7/2014 | Afriat-Staloff et al. |

FOREIGN PATENT DOCUMENTS

| EP | 0521143 A1 | 1/1993 |
| EP | 10742454 A2 | 2/2001 |
| WO | 9517166 A1 | 6/1995 |
| WO | 2005007071 A2 | 1/2005 |
| WO | 2014066850 A2 | 5/2014 |

OTHER PUBLICATIONS

Raz-Pasteur, et al., "Central Bringing Excellence in Open Access?? JSM Burns and Trauma Effect of Gamma-irradiation Sterilization on the Antibacterial Efficacy arid the Properties of a Hybrid Burn Dressing", Oct. 20, 2016, XP055539990, Retrieved from the Internet: URL:http://www.eng.tau.ac.il/-meitalz/Articles/Wound%20healing%2031.pdf, [retrieved on Jan. 9, 2019].

Mazor, et al,, "Effect of gamma-irradiation sterilization on the physical and mechanical properties of a hybrid wound dressing : Effect of Gamma-Irradiation Sterilization", Polymers for Advanced Technologies., vol. 28, No. 1, Jun. 24, 2016 (Jun. 24, 2016), pp. 41-52. (Abstract Only).

* cited by examiner

*Primary Examiner* — Mark V Stevens
(74) *Attorney, Agent, or Firm* — Corner Counsel, LLC

(57) ABSTRACT

The present disclosure relates to topical compositions comprising water, solvent, thickener, preservative and conditioning agent wherein the composition has a viscosity approximately in the range 200-6000 cP at 25° C. following exposure to gamma radiation, to use of the composition in a dressing and the use of compositions and dressings in treatment or prophylaxis of burns.

20 Claims, 11 Drawing Sheets

TOPICAL COMPOSITION FOR USE IN THE TREATMENT OF BURNS

RELATED APPLICATIONS

This application is a continuation of International Application No. PCT/IB2018/058089, which designated the United States and was filed on Oct. 18, 2018, published in English, which claims priority to Great Britain Application Nos. 1717224.8, filed Oct. 20, 2017 and 1813442.9, filed on Aug. 17, 2018. The entire teachings of the above applications are incorporated herein by reference.

The present invention relates to topical compositions comprising water, solvent, thickener, preservative and a mineral complex conditioning agent wherein the composition has a viscosity approximately in the range 200-6000 cP at 25° C. following exposure to gamma radiation, to use of the composition in a dressing and the use of compositions and dressings in treatment or prophylaxis of burns.

BACKGROUND

Approximately 1.4 million people sustain a burn injury each year in the USA alone. Of those, an estimated 54,000 to 180,000 are hospitalised. A burn is a type of injury to skin, or other tissues, caused by heat, cold, electricity, chemicals, friction, or radiation. Most burns are due to heat from hot liquids (scalds), solids or fire.

The skin is comprised of three major tissue layers: the epidermis, dermis and subcutaneous tissue. The epidermis is the outermost layer and has two components, the stratum corneum (comprised of anucleate cornified cells) and the Malpighian layers (viable cells under the stratum corneum). The stratum corneum acts as a barrier to microorganisms and toxins while allowing the body to retain water and electrolytes. The dermis is composed of dense fibroelastic connective tissue containing collagen, elastic fibres and grounds substance (an extracellular gel comprising mucopolysaccharides, salts, water and glycoproteins). The dermis is highly vascular and contains nerve networks and glands. Subcutaneous tissue is primarily areolar and fatty connective tissue and contains glands and hair follicles.

Burns that affect only the outermost skin layers are known as superficial or first-degree burns. They appear red without blisters and pain typically lasts around three days. When the injury extends into some of the underlying skin layer, it is termed a partial-thickness or second-degree burn. Blisters are frequently present and they are often very painful. Healing can require up to eight weeks and scarring may occur. In a full-thickness or third-degree burn, the injury extends to all layers of the skin. Often there is no pain and the burn area is stiff. Healing typically does not occur on its own, requiring skin grafting. A fourth-degree burn additionally involves injury to deeper tissues, such as muscle, tendons, or bone. The burn is often black and frequently leads to loss of the burned part.

When skin is burned, damage to the stratum corneum allows the invasion of microorganisms. The Langerhans cells, which mediate immune response, are also damaged. In severe burn injuries, systemic immune response can be so diminished as to make the patient susceptible to serious infection.

Treatment of burns depends on the severity of the burn. Superficial burns may be managed with little more than simple pain medication, while major burns may require prolonged treatment in specialised burn centres. Early cooling (within 30 minutes of the burn), typically with tap water, reduces burn depth and pain, but care must be taken as over-cooling can result in hypothermia. However, water is frequently not available, either at the site of the injury or in sufficient quantities. Partial-thickness burns may require cleaning with soap and water, followed by dressings. Full-thickness burns usually require surgical treatments, such as skin grafting.

The progression of burn injuries and the body's response to (thermal) burns is summarised in Edlich et al (2017) http://emedicine.medscape.com/article/1278244-overview#showall.

Many of the direct health effects of a burn are secondary to disruption in the normal functioning of the skin. They include disruption of the skin's sensation, ability to prevent water loss through evaporation and ability to control body temperature. Disruption of cell membranes causes cells to lose potassium to the spaces outside the cell and to take up water and sodium.

In large burns (over 30% of the total body surface area), there is a significant inflammatory response. This results in increased leakage of fluid from the capillaries, and subsequent tissue oedema. This causes overall blood volume loss, with the remaining blood suffering significant plasma loss, making the blood more concentrated. Poor blood flow to organs such as the kidneys and gastrointestinal tract may result in renal failure and stomach ulcers.

Wound healing progresses via three overlapping phases: inflammation, granulation and remodelling. Following a cutaneous injury, a blood clot forms and inflammatory cells infiltrate the wound, secreting cytokines and growth factors. During granulation, fibroblasts and other cells differentiate into myofibroblast which deposit extracellular matrix proteins. At the same time, angiogenesis occurs and keratinocytes proliferate and migrate to close the wound. In the remodelling phase apoptosis eliminates myofibroblasts and extraneous blood vessels and the extracellular matrix is remodelled to resemble the original tissue. Dysregulation of the remodelling phase leads to the formation of scar tissue (fibrosis).

The healing of burns progressing in essentially the same manner as all cutaneous injuries. However, the main difference is the amount of necrotic tissue, that is, tissue which is damaged beyond repair that occurs in a burn versus a cut (for example).

It is desirable to save as much of the damaged and inflamed tissue surrounding the necrotic tissue as possible following a burn and in doing so improve and speed up the wound healing ability of surrounding cells to recuperate and form a protective barrier. This allows the healing process to begin faster and improves the healing process.

It is important that any dressing applied to a burn be sterile. Irradiation is a common method of sterilising, typically employing gamma radiation. Sterilisation by gamma irradiation is aimed at reducing the bioburden (that is, the CFUs). Unfortunately, it is not uncommon for a composition or formulation to lose its integrity following irradiation, for example, a composition may become discoloured or less viscous or active ingredients be denatured. It can be a significant challenge to formulate a composition that is resistant to irradiation.

Patent EP0521143 discloses a burn dressing that can be applied to a burn in place of cool water. The dressing comprises a composition comprising tea tree oil and a carrier which is a two-layer non-woven material. The product is known to be suitable for treatment of both wet and dry burns since they stop the burning process, cool the burned area, relieve pain, prevent further injury and do not contribute to hypothermia or interfere with debridement (removal of damaged tissue or foreign objects from a wound). There are no active ingredients within the composition. The dressing conforms to the uneven burn surface and draws the heat out of a burn by spreading it over the whole gel surface.

Thus, there is a requirement for a composition suitable for application to a burn or a burn dressing that can be applied immediately following a burn injury to cool the burn whilst providing long term benefits to improve wound healing. It is further essential that the composition or dressing be sterile or sterilisable, preferably by means of gamma irradiation.

SUMMARY OF INVENTION

In a first aspect there is provided a topical composition comprising water, solvent, thickener, preservative and a mineral complex conditioning agent wherein the composition has a viscosity approximately in the range 200-6000 cPs at 25° C. following exposure to gamma radiation.

The topical composition has particular benefits for the treatment or prophylaxis of burns.

Advantageously, a composition comprising water, solvent, thickener, preservative and mineral complex conditioning agent is robust during irradiation to sterilise the composition or dressing when the composition is absorbed onto a dressing material. For example, using gamma radiation the composition is substantially unchanged following irradiation. Specifically, the composition following irradiation is a slightly viscous formulation able to sit on the skin following application to a discrete area or to be absorbed onto a dressing material.

In one embodiment there is provided a composition for primary treatment of burns.

Primary treatment as employed herein means treatment immediately following or shortly after a burn, for example within a few seconds to a few hours of the burn, such as within 11, 10, 9, 8, 7, 6, 5, 4, 3, 2 or 1 hour or less, particularly within less than 1 hour.

In one embodiment there is provided a composition for moisturising and maintaining the integrity of the affected skin.

In a further aspect there is provided a topical composition according to the disclosure for use as a medicament.

In a further aspect there is provided a topical composition according to the invention for use in the treatment or prophylaxis of burns.

In a yet further aspect there is provided a burn dressing comprising a topical composition according to the invention and a dressing material.

In a further aspect there is provided a method of sterilising a topical composition or a burn dressing according to the invention comprising applying gamma radiation of approximately 25.0 to 44.5 kGy to the composition or dressing.

In a yet further aspect there is provided a composition or a burn dressing according to the disclosure which has been sterilised using the method of the disclosure.

In a further aspect there is provided a kit of parts comprising a composition according to the disclosure and a dressing material.

In a yet further aspect there is provided a method of prophylaxis or treatment of a burn comprising the step of applying a topical composition or a burn dressing according to the invention to skin in need thereof.

The present disclosure for the first time provides a specialised and safe composition or dressing for soothing and promoting healing and regeneration of burn damaged tissue.

DESCRIPTION

Figure 1:
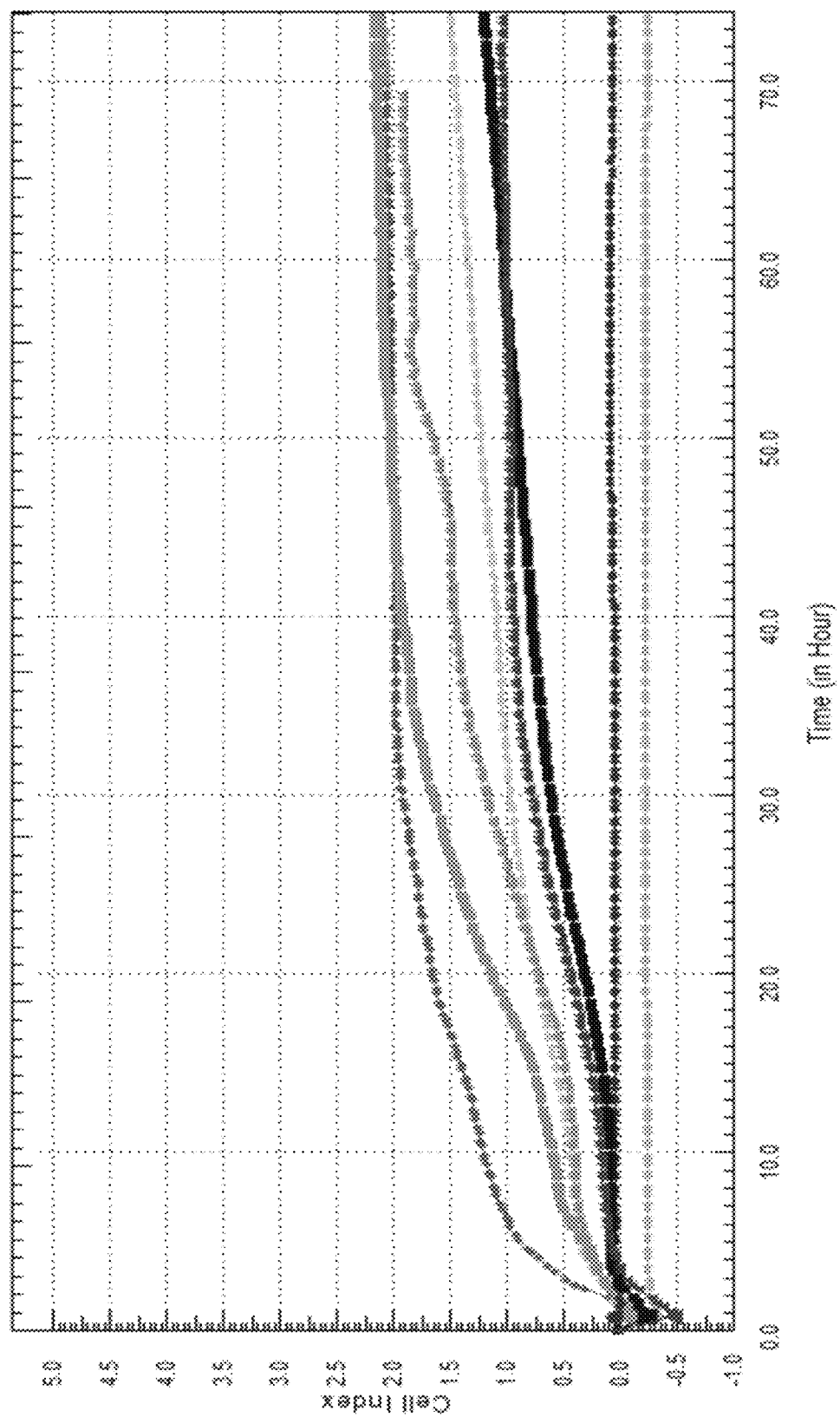
FIG. 1 shows the results of a wound healing assay—Human Primary Dermal Fibroblast data plot Cell index v time.

Burn as employed herein means an injury to skin, or other tissues, caused by heat, cold, electricity, chemicals, friction, or radiation. Compositions of the present disclosure are particularly beneficial in the treatment and prophylaxis of thermal and radiation burns although they can be employed in the treatment of any burn, including chemical burns.

In one embodiment the composition is suitable for the treatment or prophylaxis of burns, such as thermal or radiation burns, particularly thermal burns.

In one embodiment there is provided a composition for use in the treatment or prophylaxis of burns, such as thermal or radiation burns, particularly thermal burns.

As employed herein thermal burns refers to burns that are not chemical or radiation burns.

In one embodiment there is provided a composition for use in the prophylaxis of radiation burns.

Prophylaxis as employed herein refers to the prevention of condition aimed at stopping the condition developing or progressing, such as a burn or burns.

Treatment as employed herein refers to the reversal of a condition, amelioration or relief of symptoms associated with a condition or prevention of further development/worsening of a condition, such as a burn or burns.

Composition

In one embodiment there is provided a topical composition comprising water, solvent, thickener, preservative and mineral complex conditioning agent wherein the composition has a viscosity approximately in the range 200-6000 cP at 25° C. following exposure to gamma radiation.

Topical composition as employed herein means preparation that is applied to the surface of the body, such as the skin, including but not limited to a cream, foam, ointment, paste, lotion or gel, including a hydrogel.

In one embodiment the topical composition is a fluid or a gel.

Water as employed herein typically refers to purified water that has been cleaned and/or filtered to be suitable for topical application. Water may refer to tap water, purified water, sterile water, halogenated water (especially chlorinated water), and mixtures thereof. As employed herein, water has a heat-absorbing function, aimed at cooling the sensation of heat in the skin following a burn. The water also acts as a solvent. Water as employed herein has the CAS number 7732-18-5 as defined by the chemical abstract service.

In one embodiment the water is purified water. In one embodiment the water is present at approximately 85-95% w/w of the total composition, such as approximately 85.5, 86, 86.5, 87, 87.5, 88, 88.5, 89.5, 90, 90.5, 91, 91.5, 92, 92.5, 93, 93.5, 94 or 94.5% w/w of the total composition, for example approximately 89.45% w/w of the total composition. In one embodiment, the balance of the composition, following addition of other components, is water.

Solvent as employed herein means a substance (a liquid) that dissolves a solute (a chemically distinct liquid, solid or gas), resulting in a solution.

In one embodiment the solvent is present at approximately 5-10% w/w of the total composition, such as approximately 6, 7, 8 or 9% w/w of the total composition, for example approximately 8% w/w of the total composition.

In one embodiment the solvent is propanediol. In one embodiment the propanediol comprises approximately 5-10% w/w of the total composition, such as approximately 6, 7, 8 or 9% w/w of the total composition, for example approximately 8% w/w of the total composition.

Propanediol as employed herein means 1,3-propanediol, a chemical according to formula (I)

(I)

Propanediol as employed herein has the CAS number 504-63-2.

Thickener or thickening agent as employed herein is an ingredient or ingredients that increase the viscosity of a composition without substantially altering its other properties. Examples of thickening agents include polysaccharides such as gums, starches, in particular corn starch, carbomers, gelling agents and acrylates such as sodium acryloyldimethyltaurate/VP crosspolymer (Aristoflex AVS®).

In one embodiment the thickener comprises approximately 0.5-1.0% w/w of the total composition, such as approximately 0.55, 0.6, 0.65, 0.7, 0.75, 0.8, 0.85, 0.9 or 0.95% w/w of the total composition, for example approximately 0.8% w/w of the total composition.

In one embodiment the thickener is sodium acryloyldimethyltaurate/VP crosspolymer. Sodium acryloyldimethyltaurate/VP crosspolymer as employed herein has the CAS number 1176663-96-9. In one embodiment the sodium acryloyldimethyltaurate/VP crosspolymer comprises approximately 0.5-1.0% w/w of the total composition, such as approximately 0.55, 0.6, 0.65, 0.7, 0.75, 0.8, 0.85, 0.9 or 0.95% w/w of the total composition, for example approximately 0.8% w/w of the total composition.

Preservative as employed herein refers to a substance that prevents decomposition or contamination either by microorganisms or by chemical change. Typical preservatives suitable for topical compositions include, but are not limited to, phenoxyethanol, ethylhexylglycerine, caprylyl glycol, chlorphenesin, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, other examples include, esters of parahydroxybenzoic acid; and other anti-microbial agents such as chlorhexidine, chlorocresol, benzoic acid and polymyxin.

In one embodiment the preservative comprises approximately 0.5-2.0% w/w of the total composition, such as approximately 0.55, 0.6, 0.65, 0.7, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9 or 1.95% w/w of the total composition, for example approximately 1.5% w/w of the total composition.

In one embodiment the composition comprises one or more preservatives from the group consisting: phenoxyethanol and caprylyl glycol and chlorphenesin (commercially known as Mikrokill®COS) and (PHMB) polyaminopropyl biguanide.

In one embodiment the preservative is phenoxyethanol and caprylyl glycol and chlorphenesin (Mikrokill®) and (PHMB) polyaminopropyl biguanide.

In one embodiment the phenoxyethanol and caprylyl glycol and chlorphenesin (Mikrokill®COS) comprises approximately 0.5-1.5% w/w of the total composition, such as approximately 0.55, 0.6, 0.65, 0.7, 0.75, 0.8, 0.85, 0.9, 0.95, 1.0, 1.05, 1.1, 1.15, 1.2, 1.25, 1.3, 1.35, 1.4 or 1.45% w/w of the total composition, for example approximately 1.0% w/w of the total composition.

As employed herein phenoxyethanol & caprylyl glycol & chlorphenesin is the INCI name for Mikrokill®COS and has the CAS number 122-99-6/1117-86-8/104-29-0.

The composition may comprise approximately 0.25-0.75% (PHMB) polyaminopropyl biguanide, in particular approximately 0.5% (PHMB) polyaminopropyl biguanide.

The composition may comprise approximately 0.05-0.15% (PHMB) polyaminopropyl biguanide, in particular approximately 0.1% (PHMB) polyaminopropyl biguanide.

In one embodiment the (PHMB) polyaminopropyl biguanide comprises approximately 0.25-0.75% w/w of the total composition, such as 0.3, 0.35, 0.4, 0.45, 0.5, 0.55, 0.6, 0.65 or 0.7% w/w of the total composition, for example approximately 0.5% w/w of the total composition. (PHMB) polyaminopropyl biguanide as employed herein has the CAS number 133029-32-0/27083-27-8. polyaminopropyl biguanide is the INCI name. PHMB (polyhexamethylene biguanide) is the chemical name. In one embodiment the (PHMB) polyaminopropyl biguanide is provided as a 20% solution, thus 0.5% of the solution contains 0.1% (PHMB) polyaminopropyl biguanide on a pure basis.

In one embodiment the (PHMB) polyaminopropyl biguanide comprises approximately 0.05-0.15% w/w of the total composition, such as 0.06, 0.07, 0.08, 0.09, 0.1, 0.11, 0.12, 0.13 or 0.14% w/w of the total composition, for example approximately 0.1% w/w of the total composition. (PHMB) polyaminopropyl biguanide as employed herein has the CAS number 133029-32-0/27083-27-8. polyaminopropyl biguanide is the INCI name. PHMB (polyhexamethylene biguanide) is the chemical name. Typically, the (PHMB) polyaminopropyl biguanide is provided as a 20% solution, thus 0.1% of the solution contains 0.02% (PHMB) polyaminopropyl biguanide on a pure basis.

In one embodiment there is provided a topical composition comprising approximately 1.0% w/w phenoxyethanol and caprylyl glycol and chlorphenesin plus an additional approximately 0.5% w/w (PHMB) polyaminopropyl biguanide (20% solution).

In one embodiment there is provided a topical composition comprising approximately 1.0% w/w phenoxyethanol and caprylyl glycol and chlorphenesin plus an additional approximately 0.1% w/w (PHMB) polyaminopropyl biguanide (20% solution).

Mineral complex conditioning agent as employed herein means an agent designed to improve the condition of the skin.

In one embodiment the mineral complex conditioning agent comprises approximately 0.1-1.0% w/w of the total composition, such as approximately 0.15, 0.2, 0.25, 0.3, 0.35, 0.4, 0.45, 0.5, 0.55, 0.6, 0.65, 0.7, 0.75, 0.8, 0.85, 0.9 or 0.95% w/w of the total composition, for example approximately 0.25% w/w of the total composition.

In some embodiments the conditioning agent is a mineral complex. In one embodiment the mineral complex comprises approximately 0.1-1.0% w/w of the total composition, such as approximately 0.15, 0.2, 0.25, 0.3, 0.35, 0.4, 0.45, 0.5, 0.55, 0.6, 0.65, 0.7, 0.75, 0.8, 0.85, 0.9 or 0.95% w/w of the total composition, for example approximately 0.25% w/w of the total composition.

Mineral complex as employed herein refers to a complex of several minerals, typically including, but not limited to magnesium, potassium, sodium, boron, calcium. The conditioning agent/mineral complex is described in further detail below.

Viscosity as employed herein is a measure of a fluid's resistance to flow. It corresponds to a notional "thickness" of a liquid and is measured in cP (centipoise). Centipoise is a measure of viscosity on the CGS (centimetre gram second) scale. Water has a viscosity of 1 cP at 20° C. Viscosity can be measured using a Brookfield viscometer, such as a Brookfield DV II Pro. Generally, viscosity is measured at room temperature, such as 20 to 25° C., preferably 25° C.

In one embodiment there is provided a topical composition with a viscosity (at approximately 25° C.) in the range approximately 100 to 6000 cP, such as approximately 100, 150, 200, 250, 300, 350, 400, 450, 500, 550, 600, 650, 700, 750, 800, 850, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800 or 5900 cP, for example approximately 200-6000 cP.

In one embodiment the composition has a viscosity in the range 200 to 6000 cP measure using spindle #63 spindle @ 12 RPM.

As employed herein, in relation to the constituents of the composition, all % are % w/w of the total composition.

Exposure to gamma radiation as employed herein means exposure to electromagnetic radiation typically having energy above 100 keV, frequencies above 10 exahertz (or >1019 Hz) and wavelengths less than 10 picometers ($10^{-11}$ m). Typically, the gamma radiation is employed as irradiation to sterilise the composition or dressing.

In one embodiment the gamma radiation sterilises the composition or dressing. In one embodiment the gamma radiation is bacteriostatic. In one embodiment the gamma radiation is fungistatic. In one embodiment the gamma radiation reduces or eliminates the bioburden of the composition or dressing.

In one embodiment the gamma irradiation is cobalt 60 irradiation.

In one embodiment the gamma radiation is irradiation at approximately 20-50 kGy, such as approximately 21, 22, 23, 24, 25, 26, 27, 28, 29, 30, 31, 32, 33, 34, 35, 36, 37, 38, 39, 40, 41, 42, 43, 44, 45, 46, 47, 48 or 49 kGy, for example approximately 25-44.5 kGy or 25 kGy or more.

In one embodiment there is provided a composition comprising or consisting approximately: 85-95% purified water, 5-10% solvent, 0.5-1.0% thickener, 0.5-2.0% preservative, 0.1-1.0% mineral complex conditioning agent wherein each % means % w/w of the total composition.

In one embodiment there is provided a composition consisting essentially of 89.45% purified water, 8% propanediol, 0.8% sodium acryloyldimethyltaurate/VP crosspolymer, 1% phenoxyethanol and caprylyl glycol and chlorphenesin, 0.25% mineral complex and 0.5% (PHMB) polyaminopropyl biguanide (20% solution). In one embodiment the viscosity of the composition is approximately in the range 200 to 6000 cP.

In one embodiment there is provided a composition consisting essentially of 8% propanediol, 0.8% sodium acryloyldimethyltaurate/VP crosspolymer, 1% phenoxyethanol and caprylyl glycol and chlorphenesin, 0.25% mineral complex and 0.1% (PHMB) polyaminopropyl biguanide (20% solution) and purified water to make to 100%, such as approximately 89.85% purified water. In one embodiment the viscosity of the composition is approximately in the range 200 to 6000 cP.

The high water content of the composition enables it to absorb heat from the skin. Whilst not wishing to be bound by theory, the present inventors believe that this may help to reduce the development of burn by reducing the layers of skin cells permeated by the heat associated with burns.

In one embodiment the composition has a specific gravity of approximately 1.000±0.05 at 25° C.

In one embodiment the composition has a pH of approximately 5.5-7.5 at 25° C., such as approximately 5.0, 5.5, 6.5, 6.5 or 7.0, for example approximately 5.0-7.0.

In one embodiment the composition has a pH of approximately 4.0-6.5 at 25° C., such as approximately 4.5, 5.0, 5.5 or 6.0, for example approximately 4.0-6.5.

In one embodiment the topical composition is a fluid.

Fluid as employed herein means a low viscosity topical composition for application to unbroken skin. By contrast, creams and gels, including hydrogels, have a higher viscosity.

Advantageously, a lower viscosity means that the fluid is more easily absorbed by the skin and is easier to spread on the skin because it is less likely to drag the skin surface. This can be particularly useful where the patient is suffering pain or loss of skin integrity at the treatment site.

In one embodiment the composition is cooling.

In one embodiment the composition relieves pain.

In one embodiment the composition hydrates the skin.

A critical aspect of the present disclosure is the absorption of heat from the skin by the composition.

Thus, a critical aspect of the present disclosure is the reduction of the loss of skin fluid/moisture and structure by the composition.

In one embodiment there is provided a composition according to the disclosure for use as a medicament.

In one embodiment there is provided a composition according to the disclosure for use in the treatment or prophylaxis of burns. In one embodiment the burn is a thermal burn. In one embodiment the burn is a radiation burn. In one embodiment the burn is a chemical burn.

In one embodiment treatment with the composition relieves pain.

In one embodiment treatment with the composition reduces burning.

In one embodiment treatment with the composition reduces itching.

In one embodiment the composition is antimicrobial. In one embodiment the composition is antibacterial. In one embodiment the composition is antifungal.

As employed herein antimicrobial means that the composition is microbistatic or microbicidal. That is, it hinders the growth of, or kills microbes, including bacteria, fungi, viruses, protozoa, algae, amoebae and slime molds within the composition.

In one embodiment the composition reduces the depth of a burn.

In one embodiment the composition accelerates healing of the burn.

In one embodiment the composition reduces tissue necrosis.

In one embodiment the composition has substantially no oral toxicity.

In one embodiment there is provided a composition comprising water and one or more ingredients from the list consisting: propanediol, sodium acryloyldimethyltaurate/VP crosspolymer, phenoxyethanol and caprylyl glycol and chlorphenesin, mineral complex and (PHMB) polyaminopropyl biguanide. Optionally the composition has a viscosity in the range 200-6000 cP. Optionally the viscosity of the composition is measured following exposure to gamma radiation.

Mineral Complex Conditioning Agent

Conditioning agents may have beneficial properties for wound healing. Without wishing to be bound by theory, it is believed that, following a burn injury, the body withdraws minerals from the skin it considers to be lost (that is, skin that will become necrotic). By replacing those minerals, in a bioavailable form, externally, it may be possible to save more of the skin from becoming necrotic and hence lost, thus requiring grafting therapy, or developing scarring.

Thus, in one embodiment the conditioning agent is a mineral complex conditioning agent. In one embodiment the mineral complex comprises bioavailable minerals, such as ion, free ions, elemental, or bound minerals, for example free ions.

In one embodiment the mineral complex comprises magnesium, potassium, sodium, boron, calcium and optionally one or more from the group consisting: copper, nickel, silicon, zinc, aluminium, arsenic, barium, cadmium, cobalt, chromium, iron, mercury, manganese, lead, antimony, selenium, tin, strontium, titanium and vanadium.

In one embodiment the mineral complex is sea water extract. As employed herein sea water extract is the INCI name.

As employed herein sea water extract may be harvested from a deep sea source. Typically, the sea water extract is a concentrated solution of deep sea water minerals wherein the amount of sodium and/or chlorine has been reduced and/or substantially eliminated.

In one embodiment the sea water extract is dead sea salt, Cornish sea salt, Maldon sea salt, Himalayan sea salt and the like.

In one embodiment the mineral complex is Epsom salts.

In one embodiment the sea water extract is the INCI and IUPAC name.

In one embodiment the sea water extract is Deep Sea Water provided by Morechem. In one embodiment the sea water extract is Eau de Source Marine SC, Ocaline or Ocaline XP provided by Soliance (Givaudan) or the like.

In one embodiment the mineral complex conditioning agent is added to the composition in liquid form, such as a concentrate of sea water.

In one embodiment the mineral complex conditioning agent is added to the composition in dried form. For example, as dried, concentrate of sea water.

In one embodiment the mineral complex does not comprise bound minerals such a magnesium sulphate/oxide/citrate.

In one embodiment the mineral complex comprises free magnesium, such a $Mg^{2+}$ ions. In one embodiment the major component of the mineral complex is magnesium.

In one embodiment the mineral complex comprises potassium, such as free potassium, such as $K^+$ ions.

In one embodiment the mineral complex comprises sodium, such as free sodium, such as $Na^+$ ions.

In one embodiment the mineral complex comprises boron, such as free boron, such as boron anions or boron cations.

In one embodiment the mineral complex comprises calcium, for example free calcium, such as $Ca^{2+}$ ions.

In one embodiment the mineral complex provides bioavailable minerals, such as magnesium.

In one embodiment the mineral complex has substantially no chloride or chlorine.

In one embodiment the sea water extract is Oriel sea water extract (orielmarineextracts.com) provided by Oriel Sea Salt Co.

In one embodiment the sea water extract has a pH of approximately 7 to 8, such as approximately 7.4.

In one embodiment the sea water extract has a density of approximately 40%.

Table 1 shows the components of sea water.

TABLE 1

| Element | Atomic weight | ppm | Element | Atomic weight | ppm |
|---|---|---|---|---|---|
| Hydrogen H2O | 1.0079 | 110,000 | Molybdenum Mo | 0.09594 | 0.01 |
| Oxygen H2O | 15.999 | 883,000 | Ruthenium Ru | 101.07 | 0.0000007 |
| Sodium NaCl | 22.989 | 10,800 | Rhodium Rh | 102.905 | . |

TABLE 1-continued

| Element | Atomic weight | ppm | Element | Atomic weight | ppm |
|---|---|---|---|---|---|
| Chlorine NaCl | 35.453 | 19,400 | Palladium Pd | 106.4 | |
| Magnesium Mg | 24.312 | 1,290 | Argentum (silver) Ag | 107.870 | 0.00028 |
| Sulfur S | 32.064 | 904 | Cadmium Cd | 112.4 | 0.00011 |
| Potassium K | 39.102 | 392 | Indium In | 114.82 | . |
| Calcium Ca | 10.080 | 411 | Stannum (tin) Sn | 118.69 | 0.00081 |
| Bromine Br | 79.909 | 67.3 | Antimony Sb | 121.75 | 0.00033 |
| Helium He | 4.0026 | 0.0000072 | Tellurium Te | 127.6 | . |
| Lithium Li | 6.94 | 0.170 | Iodine I | 166.904 | 0.064 |
| Beryllium Be | 9.0133 | 0.0000006 | Xenon Xe | 131.30 | 0.000047 |
| Boron B | 10.811 | 4.450 | Cesium Cs | 132.905 | 0.0003 |
| Carbon C | 12.011 | 28.0 | Barium Ba | 137.34 | 0.021 |
| Nitrogen ion | 14.007 | 15.5 | Lanthanum La | 138.91 | 0.0000029 |
| Fluorine F | 18.998 | 13 | Cerium Ce | 140.12 | 0.0000012 |
| Neon Ne | 20.183 | 0.00012 | Praesodymium Pr | 140.907 | 0.00000064 |
| Aluminium Al | 26.982 | 0.001 | Neodymium Nd | 144.24 | 0.0000028 |
| Silicon Si | 28.086 | 2.9 | Samarium Sm | 150.35 | 0.00000045 |
| Phosphorus P | 30.974 | 0.088 | Europium Eu | 151.96 | 0.0000013 |
| Argon Ar | 39.948 | 0.450 | Gadolinium Gd | 157.25 | 0.0000007 |
| Scandium Sc | 44.956 | <0.000004 | Terbium Tb | 158.924 | 0.00000014 |
| Titanium Ti | 47.900 | 0.001 | Dysprosium Dy | 162.50 | 0.00000091 |
| Vanadium V | 50.942 | 0.0019 | Holmium Ho | 164.930 | 0.00000022 |
| Chromium Cr | 51.996 | 0.0002 | Erbium Er | 167.26 | 0.00000087 |
| Manganese Mn | 54.938 | 0.0004 | Thulium Tm | 168.934 | 0.00000017 |
| Ferrum (Iron) Fe | 55.847 | 0.0034 | Ytterbium Yb | 173.04 | 0.00000082 |
| Cobalt Co | 58.933 | 0.00039 | Lutetium Lu | 174.97 | 0.00000015 |
| Nickel Ni | 58.710 | 0.0066 | Hafnium Hf | 178.49 | <0.000008 |
| Copper Cu | 63.54 | 0.0009 | Tantalum Ta | 180.948 | <0.0000025 |
| Zinc Zn | 65.37 | 0.005 | Tungsten W | 183.85 | <0.000001 |
| Gallium Ga | 69.72 | 0.00003 | Rhenium Re | 186.2 | 0.0000084 |
| Germanium Ge | 72.59 | 0.00006 | Osmium Os | 190.2 | . |
| Arsenic As | 74.922 | 0.0026 | Iridium Ir | 192.2 | . |
| Selenium Se | 78.96 | 0.0009 | Platinum Pt | 195.09 | . |
| Krypton Kr | 83.80 | 0.00021 | Aurum (gold) Au | 196.967 | 0.000011 |
| Rubidium Rb | 85.47 | 0.120 | Mercury Hg | 200.59 | 0.00015 |
| Strontium Sr | 87.62 | 8.1 | Thallium Tl | 204.37 | . |
| Yttrium Y | 88.905 | 0.000013 | Lead Pb | 207.19 | 0.0003 |
| Zirconium Zr | 91.22 | 0.000026 | Bismuth Bi | 208.980 | 0.00002 |
| Niobium Nb | 92.906 | 0.000015 | Thorium Th | 232.04 | 0.0000004 |
| | | | Uranium U | 238.03 | 0.0033 |
| | | | Plutonimu Pu | (244) | . |

In one embodiment the mineral complex comprises approximately: 66% magnesium, 23.8% potassium, 9.8% sodium, 0.002% boron, 0.0006% calcium, 0.00002% copper, 0.000012% nickel, 0.0000087% silicon and 0.000001% zinc. Wherein approximately is defined to be ±15%. In one embodiment the mineral complex further comprises trace elements. In one embodiment the trace elements include one or more from the group: aluminium, arsenic, barium, cadmium, cobalt, chromium, iron, mercury, manganese, lead, antimony, selenium, tin, strontium, titanium and vanadium. In one embodiment the trace elements may be any element selected from table 1.

In one embodiment the mineral complex comprises one or more minerals according to table 1.

Dressing Material

A burn dressing in accordance with the present disclosure is formed by impregnating a suitable dressing material with the composition of the disclosure.

Dressing material as employed herein means a fabric carrier capable of holding a chosen volume of composition. Preferably the dressing material is a non-woven synthetic material that will hold a substantial quantity of the composition to apply an effective amount of the composition to a burn. The dressing material must be capable of being sterilised, typically by irradiation, such as gamma irradiation and non-irritating to burned skin.

In one embodiment there is provided a burn dressing comprising a topical composition according to the disclosure and a dressing material.

In one embodiment the dressing material comprises thermal bonded, non-woven material.

In one embodiment the dressing material is polyester, PET (polyethylene terephthalate) or the like, such as medical grade non-woven 100% polyester fabric, for example polypropylene or rayon.

Thermal bonded as employed herein means a fabric wherein heat energy is used to stimulate an adhesive, which in turn flows to thermoplastic fibre juncture and interlocks the fibres upon cooling.

Non-woven as employed herein refers to sheet or web structures bonded together by entangling fibre or filaments (and by perforating films) mechanically, thermally or chemically. They are flat, porous sheets that are made directly from separate fibres or from molten plastic or plastic film.

In one embodiment the dressing material comprises super absorbent material, such as super absorbent fibre.

Super absorbent materials have an absorbent capacity of several times their weight. Super absorbent fibres are fibrous form of super absorbent material which can be incorporated into woven or non-woven materials.

In one embodiment the dressing material comprises polypropylene fibre and rayon fibre.

In one embodiment the dressing material comprises super absorbent fibre, polypropylene fibre and rayon fibre.

In one embodiment the dressing material comprises approximately 10-40% super absorbent fibre, such as approximately 11, 12, 13, 14, 15, 16, 17, 18, 19, 20, 21, 22, 23, 24, 25, 26, 27, 28, 29, 30, 31, 32, 33, 34, 35, 36, 37, 38 or 39% super absorbent fibre, for example approximately 20% super absorbent fibre.

In one embodiment the dressing material has one of more of the properties selected from the group consisting: a weight of approximately 50 gsm, a thickness of approximately 0.63 mm, a tensile strength of approximately 4.2 N or 24.3 N, an absorbent capacity of approximately 22.7 g/g and an absorbent volume of approximately >1150 gsm.

In one embodiment the dressing material is type 2741 fabric as provided by Technical Absorbents.

In one embodiment the dressing has a width of approximately 5 cm to 50 cm and a length of approximately 5 cm to 50 cm. Such as approximately 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 cm width and/or length.

In one embodiment the dressing material holds approximately 15 to 30 grams of composition per gram, such as approximately 16, 17, 18, 19, 20, 21, 22, 23, 24, 25, 26, 27, 28 or 29 grams of composition per gram, for example approximately 22.7 g/g.

In one embodiment the dressing material holds approximately 1000 to 2000 g of composition per square metre of dressing material, such as approximately 1100, 1200, 1300, 1400, 1500, 1600, 1700, 1800 or 1900 g of composition per square metre of dressing material. For example, approximately 1674 g of composition per square metre of dressing material.

In one embodiment the dressing is of shape and dimension suitable for application to the face. In such embodiment the dressing may have slots or holes for the eyes and/or nose and/or mouth.

In one embodiment the dressing material has pockets in which the composition may be placed. For examples, see EP0521143 which is incorporated herein by reference.

Sterilisation

In one embodiment the composition or dressing is sterilised, for example by heat (such as by steam or dry heat), irradiation (such as electron beam or gamma radiation), gas (such as ethylene oxide or formaldehyde) or low temperature oxidative sterilisation (such as vaporised hydrogen peroxide, hydrogen peroxide/gas plasma).

In one embodiment the composition or dressing is sterilised by gamma irradiation.

In one embodiment the gamma irradiation is cobalt 60 or caesium 137 radiation, particularly cobalt 60 radiation.

In one embodiment the composition or dressing is irradiated to meet 10E6 sterility assurance level (SAL).

In one embodiment the sterilisation method is AAMI 11137-2 compliant.

Advantageously, compositions and dressing that have been sterilised employing the method have substantially zero bioburden. That is, they have zero CFUs. Such as no microbe that can replicate or grow.

Packaging

In one embodiment the burn dressing as disclosed herein is packaged into a storage pouch. Advantageously, the storage pouch permits the dressing to remain sterile and be easily transported, for example is a first aid kit or medical kit, such as for use by a paramedic.

Typically, the storage pouch has a three-layer construction of a layer of polyester having a layer of aluminium thereon and a layer of, for example, Scotchpak® heat sealable polyester film thereof. The three layers are adhered with adhesive.

The compositions, dressings and methods of the present disclosure when employed help maintain skin integrity, minimise the deleterious effects of burns and reduce opportunistic infections that may occur when skin is damaged.

The maintenance of moisture around the burn may also minimise scarring and prevent reduced flexibility in the area of skin damage. This is advantageous because it may reduce pain associated with scar tissue and avoids skin thickening and reduced skin elasticity which, in skin folds, can be problematic.

It is desirable to avoid skin toughness that can arise following damage to the skin because toughened skin is prone to flaking and cracking which in turn can lead to inflammation and infection.

In one embodiment damaged cells treated with the topical composition or dressing recover viability more quickly than untreated cells. In one embodiment cell viability is restored more quickly in cells treated with the topical composition or dressing.

In one embodiment there is provided a burn dressing for use in the treatment or prophylaxis of burns. Typically, the burn dressing comprises a composition as disclosed herein absorbed and carried on or in a dressing material as described herein.

Ideally the composition or dressing as described herein is applied to a burn as soon as possible following the burn. Preferably the composition or dressing is applied immediately, such as within a minute of the burn. The composition or dressing may be applied within a few hours of the burn injury.

In some situations, the composition or dressing may be applied following treatment by a medical professional. That is, the composition or dressing may be employed other than as a first aid treatment. For example, the composition or dressing may be employed for prolonged use, for example, to keep a burn wound sterile and/or hydrated. Such use of the composition or dressing supports the skin cells by providing external bioavailable minerals which, it is thought, supports the increased metabolism of the cells.

In one embodiment the composition or dressing is applied once, twice, three or four a day.

In one embodiment the composition or dressing is applied to skin, such as the area of the burn, and left for approximately 10 minutes to 36 hours, for example approximately 20, 30, 40 or 50 minutes or approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35 hours. In one embodiment the composition or dressing is applied to a burn for up to approximately 24 hours.

In one embodiment there is provided a composition or dressing for use in treatment of a burn wherein the treatment is prolonged treatment.

In one embodiment there is provided a method of prophylaxis or treatment wherein the composition or dressing is applied to a burn for approximately 24 hours. For example approximately 11, 12, 13, 14, 15, 16, 17, 18, 19, 20, 21, 22, 23, 24, 25, 26, 27, 28, 29, 30, 31, 32, 33, 34, 35 or 36 hours or more.

In one embodiment treatment with the composition or dressing continues for about 2 to 10 weeks following each burn injury, such as 3, 4, 5, 6, 7, 8, or 9 weeks following burn injury.

Typically, the composition or dressing is changed daily and a new composition or dressing according to the disclosure applied to the burn injury.

In one embodiment the composition or dressing provide bioavailable minerals to the skin. In one embodiment the minerals include magnesium. It is believed that bioavailable magnesium may help prevent magnesium depletion which is known to be a complicating factor in burn injuries. In one embodiment the minerals include calcium.

In one embodiment the composition or dressing promote faster healing of the burn wound. In one embodiment use of the composition or dressing results in reduced scarring.

In one embodiment there is provided a composition or dressing as disclosed herein for use in reducing scarring.

Thus, there is provided a composition or dressing for direct application to a burn wound. The dressing can be employed to cover the entire burn. Debridement of the burn is not necessary prior to application of the composition or dressing. The composition rapidly penetrates clothing and wets, cools and soothes a burn. The burn is wet, cooled and soothed, not only on the surface but beneath the surface, thereby reducing progression of the burn. The burn dressing cools by heat transference and helps create an isothermic environment. Additionally, the composition or burn dressing helps reduce contamination of the burn by covering the burn and blocking air-borne microbes. Clothing and skin do not adhere to the burn dressing when it is removed, thereby limiting pain and skin damage when the dressing is removed.

The composition and dressing are non-toxic, water-soluble and retain properties after extended storage. Advantageously, the composition and dressing are easy to use.

In the context of this specification "comprising" is to be interpreted as "including".

Approximately, as used herein, means±10%.

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The present invention is further described by way of illustration only in the following examples:

EXAMPLES

Example 1

Following several failed attempts to formulate a composition with suitable viscosity and other properties to function as a burn treatment, the Inventors obtained stable compositions which were sent for testing to assess stability under gamma radiation.

OVERVIEW: To incorporate: Polyaminopropyl biguanide (INCI name); Chemical name: Polyhexamethylene Biguanide Hydrochloride (PHMB) and later Oriel sea mineral complex into a gel formula that can withstand the impact of gamma radiation sterilisation.

5 rounds of formulas were sent out for gamma radiations as outlined below.

Round 1 Summary: Started with our current BD (Burn Dressing) Gel with hyaluronic acid (HA) formula to which various ingredients were added.

The table below shows the key ingredients added to BD gel w/HA formula to determine their impact on gamma radiation resistance (Experiments A through L). Experiment L containing Carbopol and water only, shows that PHMB @1% (20% solution) is incompatible with Carbopol (thickening agent). The gel curdles. Carbopol is the thickening agent used in BD Gel with HA, the only experiment in round 1 to which PHMB was added.

TABLE 2

| Experiment | Key ingredients (Round 1) BD and HA plus: | Ingredient INCI/Name | Function | Discolouration following Y radiation (1-10) |
|---|---|---|---|---|
| A | Glycerin | Glycerin | Humectant | 1.2 |
| B | Propylene glycol | 1,2-Propanediol | Humectant | 1.0 |
| C | Tinoguard HS (BASF) | Sodium Benzotriazolyl Butylphenol Sulfonate | UV absorber | 4.0 |
| D | Cibafash H Liquid (BASF) | Sodium Benzotriazolyl Butylphenol Sulfonate | UV absorber | 3.5 |
| E | Tinoguard TT (BASF) | Penaerythityl Tetra-di-t-butyl Hydroxyhydrocinnamate | UV absorber | 2.5 (slightly hazy) |
| F | PHMB | Polyaminoproyl biguanide | Preservative | 3 (off white, hazy) |
| G | A, B, C, D, E | See above | See above | 3.5 (off white, hazy) |
| H | A, B, C, D, E, F | See above | See above | 1.5 |
| I | microsilver | Not sent for radiation - too dark | | |
| J | Control - additional ingredients | | | 1.2 |
| K | Control - just Carbopol and water, not irradiated | | | |
| L | Control - just Carbopol, water and trolamine | | | 6.0 |

After gamma results: Discolouration was measured on a scale of 1 (no discolouration) to 10 (intense discolouration) UV absorbers showed some discolouration; propylene glycol showed little or no change following gamma radiation.

Round 2 Summary: Since PHMB was incompatible with Carbopol, new formulas containing various other thickeners were tried. Since propylene glycol, a humectant helped, another humectant (propanediol) was tried. For all the experimental batches made, only the stable formulas were sent out for gamma radiation. Only some of round 2 formulas contain PHMB (20% solution) @0.2%

The base gel employed in experiments is water plus thickener (Natrosol or Laponite for example).

TABLE 3

| Key Ingredients (Round 2) | Ingredient INCI/Chemical Name | Function |
|---|---|---|
| Natrosol 250 HHX | Pharm hydroxyethylcellulose | Thickening agent |
| Propylene glycol | Propylene glycol (1,2-Propanediol) | humectant |
| Laponite XL 21 | Sodium Magnesium Fluorosilicate | Thickening agent |
| Propanediol | Propanediol (1,3-Propanediol) | Solvent |
| Xanthan gum | Xanthan gum | Thickening agent |
| Carrageenan | Carrageenan | Thickening agent |
| Aculyn 21 | Acrylates/Steareth-20 Methacrylate Copolymer | Thickening agent |
| Agar powder | Agar | Thickening agent |
| Poloxamer 188 | Poloxamer 188 | Surfactant/Thickening agent |
| Glycerin | Glycerin | Humectant |

Formulas with xanthan gum carrageenan, aculyn 46 N, poloxamer 188 and agar were unstable/thinned out or discoloured (thickening agents not compatible with PHMB) and therefore gels were not sent out for gamma radiation.

After Gamma Radiation Results:

Formulas containing Natrosol 250 HEX completely loss viscosity and became "water thin" but gel was not discoloured. Formulas with propylene glycol were clear but also had a pinkish hue. Formulas with propanediol remained clear; those with glycerin acquired a yellowish hue.

Round 3 Summary: For round 3 experiments, 2 new thickening agents (Sodium Carboxymethyl Cellose and Aristoflex AVS) were tested.

All the formulas in round 3 contained PHMB 0.2% (20% solution). Only stable formulas were sent out for gamma radiation.

After Gamma Radiation Results:

Formulas containing sodium carboxymethyl cellose became watery. Although the combination of Carbopol and Natrosol 250 HHX showed some promising results (Exp. G), the best result was EXP.F which contained a combination of propanediol and Aristoflex AVS.

Round 4 Summary: In round 4 experiments, Oriel sea mineral extract skin conditioner was introduced into the formulas. This ingredient lowers the viscosity of the gel. As in Round 3 experiments, PHMB was still used @ 0.2% (20% solution). Experiment F, (Round 3) having the best results from round 3 was the starting point. The level of Aristoflex AVS (thickening agent) was varied to compensate for the viscosity reducing effect of the Oriel sea mineral extract. The levels of propanediol were also varied from 5% to 12% to see what if any effect that had on the gamma radiation results as well on overall product appearance.

TABLE 4

| Experiment | Key Ingredients (Round 3) Water plus: | Ingredient INCI/Chemical Name | Function |
|---|---|---|---|
| A | Sodium Carboxymethyl Cellose and PHMB | Sodium Carboxymethyl Cellose | Thickening agent |
| B | A plus propanediol | | |
| C | B plus Mikrokill and disodium EDTA | | |
| D | A plus disodium EDTA, propylene glycol, Mikrokill | | |
| E | Disodium EDTA, propanediol, Mikrokill, PHMB, Carbopol 980, trolamine | | |
| F | Disodium EDTA, propanediol, Mikrokill, PHMB, Aristoflex AVS | Sodium Acryloyldimethyltaurate/VP Crosspolymer | Thickening agent |
| G | Disodium EDTA, propanediol, Mikrokill, PHMB, Natrosol HHX, Carbopol 980, trolamine | | |

TABLE 5

| Key Ingredients (Round 4) | Ingredient INCI/Chemical Name | Function |
| --- | --- | --- |
| Oriel Sea Mineral Extract | Sea water extract | Skin conditioning agent |
| Aristoflex AVS | Sodium Acryloyldimethyltaurate/VP Cross polymer | Thickening agent |
| Propylene glycol | Propylene glycol (1,2-Propanediol) | Solvent |
| Propanediol | Propanediol (1,3-Propanediol) | Solvent |
| Carbopol 980 | Carbomer | Thickening agent |
| Natrosol 250 HHX | Pharm hydroxyethylcellulose | Thickening agent |

Only stable formulas were sent out for gamma radiation. After Gamma Results:

All the experiments containing a combination of Aristoflex AVS, PHMB and propanediol showed good results regardless of the level of propanediol. Compositions with propanediol and Carbopol but without PHMB had good results. Compositions with propanediol/Carbopol/PHMB combination showed a significant decrease in viscosity.

Round 5 Summary: Round 5 experiments involved: (a) optimising the viscosity of the product to work more efficiently with the new absorbent material. (b) Increasing the level of PHMP from 0.2% to 0.5% (20% solution). (c) Making formulas for preservative challenge without the main preservative Microkill COS but with PHMB along with various levels of propanediol (which has preservative properties). Note: Final formula contains Microkill COS. (d) Optimising the manufacturing process.

TABLE 6

| Key Ingredients (Round 5) | Ingredient INCI/Chemical Name | Function |
| --- | --- | --- |
| Oriel Sea Mineral Extract | Sea water extract | Skin conditioning agent |
| Aristoflex AVS | Sodium Acryloyldimethyltaurate/VP Crosspolymer | Thickening agent |
| Propylene glycol | Propylene glycol (1,2-Propanediol) | Solvent |
| Propanediol | Propanediol (1,3-Propanediol) | Solvent |

In round 5, the final formula was determined from a selection of which were sent out for gamma radiation with acceptable results. All the formulas are similar except for their levels of Aristoflex AVS (thickening agent) varying from 1.0%, 0.9% and 0.8% respectively. A decision was made to go with a formula with 0.8% Aristoflex AVS (final formula), the least viscous formula.

In order to test physical integrity of the composition following gamma radiation, the viscosity at room temperature and 40° C. can be tested and compared to a control which was not irradiated.

Example 2

Wound healing progresses via three overlapping phases: inflammation, granulation and tissue remodelling. After cutaneous injury, a blood clot forms, and inflammatory cells infiltrate the wound, secreting cytokines and growth factors to promote the inflammation phase. During the granulation phase, fibroblasts and other cells differentiate into myofibroblasts, which deposit extracellular matrix (ECM) proteins. Simultaneously, angiogenesis occurs, and keratinocytes proliferate and migrate to close the wound. In the final tissue-remodelling phase, apoptosis eliminates myofibroblasts and extraneous blood vessels, and the ECM is remodelled to resemble the original tissue. Dysregulation of this last tissue remodelling phase leads to fibrosis.

In order to monitor this cytotoxicity, behaviour, impact and biofunctionality of the composition in (1) Human Vascular Endothelial Cells, (2) Human Dermal Fibroblasts and (3) Human Dermal Keratinocytes we employed an electrical-impedance based technique that monitors and quantifies in real-time the behaviour of cells, which is also amenable to high throughput. Giaever and Keese first described a technique for measuring fluctuations in impedance based on the principle of population cell growth on a specialized electrode surface. The xCELLigence instrument, established and optimised in the laboratory of Dr Ronan Murphy (Dublin City University), utilises a similar technique to measure changes in electrical impedance. Through preliminary studies and data from working with the 'mineral-complex' ingredient, we have determined protocols and conditions that are optimal for cell functionality and activation in all three cell types. For this we used a 2.5D model on e-plates. Briefly, as cells attach and spread in a culture dish covered with a gold microelectrode array that covers approximately 80% of the area on the bottom of a well. As cells attach and spread on the electrode surface, it leads to an increase in electrical impedance. The impedance is displayed as a dimensionless parameter termed cell-index, which is directly proportional to the total area of tissue-culture well that is covered by cells. Hence, the cell-index can be used to monitor many critical stages of cell behaviour such as wound healing: cell adhesion, spreading, morphological changes, detachment, proliferation, migration, apoptosis and cell density.

The standard wound healing assay was utilised in this study based on changes in electrical impedance at the electrode/cell interphase, as a population of cells migrates an advanced double chamber apparatus know as a CIM plate. Cell migration, fate, function and behaviour lead to large changes in impedance. These changes directly correlate with the wound healing capacity of the three cell types, i.e., migration and tissue/ECM remodelling by cells lead to large changes in cell impedance and vice versa. This advanced wound-healing assay involved a two-chamber system (xCELLigence CIM (cell invasion and migration) plate) to monitor and measure transmigration as well as initial surface layer disruption. This technique provides a two-fold advantage over existing methods of measuring invasion, such as Boyden chamber and matrigel assays: firstly, the Cell-Extra Cellular Matrix interactions and remodelling more closely mimics the in vivo process, and secondly, the data was obtained in real-time and is more easily quantifiable, as opposed to end-point analysis for other methods.

Dermal fibroblasts are cells that lay within the dermis layer of skin and are responsible for generating connective tissue and allowing the skin to recover from injury. Dermal fibroblasts generate and maintain the connective tissue which unites separate cell layers, particularly via the rough endoplasmic reticulum. Crucially, it is these dermal fibroblasts that produce the protein molecules, including laminin and fibronectin, which comprise the extracellular matrix (ECM). Hence, by creating the ECM between the dermis and epidermis, fibroblasts facilitate the epithelial cells of the epidermis to affix the matrix, thereby allowing the epidermal cells to effectively join together to form the top layer of the skin.

Figure 2:
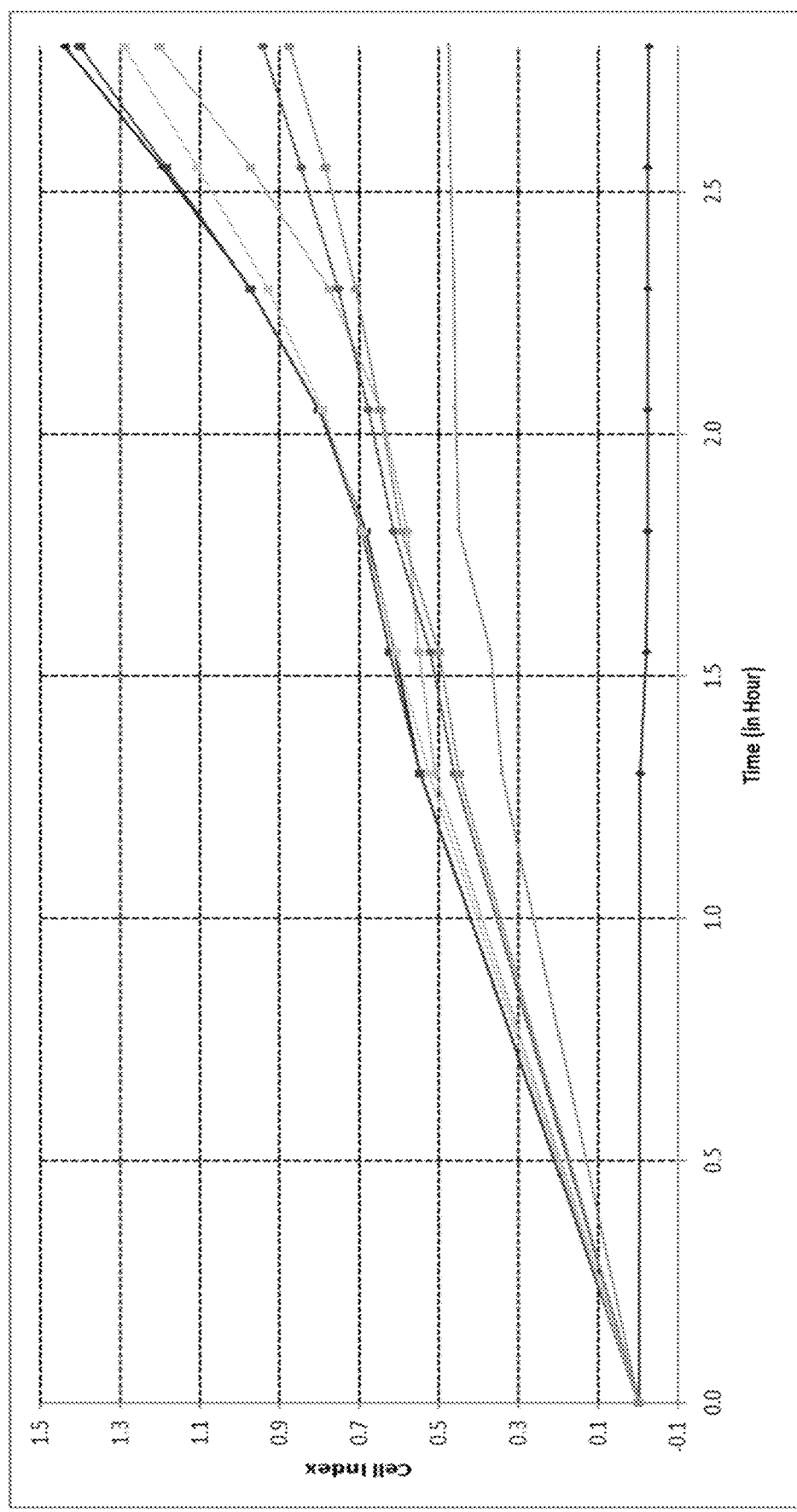
FIG. 2 shows Human Primary Keratinocyte cells cell index v time.

In our experiments, dermal fibroblast cells were grown in culture, starving them of magnesium for 24 hours before treating them to (NB105-142) & appropriate controls. Cells were seeded onto 0.32 cm2 wells of the xCELLigence real-time monitoring system, upon which, a minimal layer of ECM had been permitted to form. Cells were then allowed to adhere to the electrode surface and migrate accordingly. Results are presented In FIGS. 1 and 2.

Example 3

We employed the Wound Healing RT2 Profiler PCR Array to assess the effect of the composition on gene expression during the process outlined in Example 2. This time both fibroblast monoculture (Example 3a) and our established human LabSkin model (see Duffy Et al, 2017, Cosmetics, 4, 44) was used (Example 3b).

This array contains genes important for each of the three phases of wound healing, including ECM remodelling factors, inflammatory cytokines and chemokines, as well as growth factors and major signalling molecules. Using real-time PCR, you can easily and reliably analyse the expression of a focused panel of genes involved in wound healing, tissue injury and repair with this array. The RT2 Profiler PCR Array System is the most reliable and accurate tool for analysing the expression of a focused panel of genes using SYBR Green-based real-time PCR. It brings together the quantitative performance of real-time PCR and the multiple gene profiling capability of microarrays. Each PCR Array profiles the expression of 84 genes relevant to a specific pathway or disease state—in this case Wound Healing. Expression levels are measured by gene-specific RT2 qPCR Primer Assays optimized for simultaneous use in the PCR Array System. RT2 qPCR Primer Assays are key components in the PCR Array System. Each qPCR assay on the array is uniquely designed for use in SYBR Green real-time PCR analysis. The assay design criteria ensure that each qPCR reaction will generate single, gene-specific amplicons and prevent the co-amplification of non-specific products. The qPCR Assays used in PCR Arrays are optimised to work under standard conditions enabling a large number of genes to be assayed simultaneously. This system is specifically designed to meet the unique challenges of profiling pathway-focused sets of genes using real-time PCR. Simultaneous gene expression analyses require similar qPCR efficiencies for accurate comparison among genes. $RT^2$ qPCR Primer Assays are designed with an amplicon size ranging from 100 to 250 bp and with PCR efficiencies uniformly greater than 90%. Overall, more than 10 thermodynamic criteria are included in the design of each $RT^2$ qPCR Primer Assay to ensure the most reliable and accurate results for pathway-based gene expression analysis in the PCR Array System. The array layout is shown in Table 7 below.

TABLE 7

| Position | Ref/Seq Number | Symbol | Description |
|---|---|---|---|
| A01 | NM_001613 | ACTA2 | Actin, alpha 2, smooth muscle, aorta |
| A02 | NM_005159 | ACTC1 | Actin, alpha, cardiac muscle 1 |
| A03 | NM_001146 | ANGPT1 | Angiopoietin 1 |
| A04 | NM_002982 | CCL2 | Chemokine (C-C motif) ligand 2 |
| A05 | NM_006273 | CCL7 | Chemokine (C-C motif) ligand 7 |
| A06 | NM_000074 | CD40LG | CD40 ligand |
| A07 | NM_004360 | CDH1 | Cadherin 1, type 1, E-cadherin (epithelial) |
| A08 | NM_021110 | COL14A1 | Collagen, type XIV, alpha 1 |
| A09 | NM_000088 | COL1A1 | Collagen, type I, alpha 1 |
| A10 | NM_000089 | COL1A2 | Collagen, type I, alpha 2 |
| A11 | NM_000090 | COL3A1 | Collagen, type III, alpha 1 |
| A12 | NM_001845 | COL4A1 | Collagen, type IV, alpha 1 |
| B01 | NM_000091 | COL4A3 | Collagen, type IV, alpha 3 (Goodpasture antigen) |
| B02 | NM_000093 | COL5A1 | Collagen, type V, alpha 1 |
| B03 | NM_000393 | COL5A2 | Collagen, type V, alpha 2 |
| B04 | NM_015719 | COL5A3 | Collagen, type V, alpha 3 |
| B05 | NM_000758 | CSF2 | Colony stimulating factor 2 (granulocyte-macrophage) |
| B06 | NM_000759 | CSF3 | Colony stimulating factor 3 (granulocyte) |
| B07 | NM_001901 | CTGF | Connective tissue growth factor |
| B08 | NM_001904 | CTNNB1 | Catenin (cadherin-associated protein), beta 1, 88 kDa |
| B09 | NM_001911 | CTSG | Cathepsin G |
| B10 | NM_000396 | CTSK | Cathepsin K |
| B11 | NM_001333 | CTSV | Cathepsin L2 |
| B12 | NM_001511 | CXCL1 | Chemokine (C-X-C motif) ligand 1 (melanoma growth stimulating activity, alpha) |
| C01 | NM_005409 | CXCL11 | Chemokine (C-X-C motif) ligand 11 |
| C02 | NM_002089 | CXCL2 | Chemokine (C-X-C motif) ligand 2 |
| C03 | NM_002994 | CXCL5 | Chemokine (C-X-C motif) ligand 5 |
| C04 | NM_001963 | EGF | Epidermal growth factor |
| C05 | NM_005228 | EGFR | Epidermal growth factor receptor |
| C06 | NM_000129 | F13A1 | Coagulation factor XIII, A1 polypeptide |
| C07 | NM_001993 | F3 | Coagulation factor III (thromboplastin, tissue factor) |
| C08 | NM_000508 | FGA | Fibrinogen alpha chain |
| C09 | NM_004465 | FGF10 | Fibroblast growth factor 10 |
| C10 | NM_002006 | FGF2 | Fibroblast growth factor 2 (basic) |
| C11 | NM_002009 | FGF7 | Fibroblast growth factor 7 |

TABLE 7-continued

| Position | Ref/Seq Number | Symbol | Description |
|---|---|---|---|
| C12 | NM_001945 | HBEGF | Heparin-binding EGF-like growth factor |
| D01 | NM_000601 | HGF | Hepatocyte growth factor (hepapoietin A; scatter factor) |
| D02 | NM_000619 | IFNG | Interferon, gamma |
| D03 | NM_000618 | IGF1 | Insulin-like growth factor 1 (somatomedin C) |
| D04 | NM_000572 | IL 10 | Interleukin 10 |
| D05 | NM_000576 | IL1B | Interleukin 1, beta |
| D06 | NM_000586 | IL2 | Interleukin 2 |
| D07 | NM_000589 | IL4 | Interleukin 4 |
| D08 | NM_000600 | IL6 | Interleukin 6 (interferon, beta 2) |
| D09 | NM_002184 | IL6ST | Interleukin 6 signal transducer (gp130, oncostatin M receptor) |
| D10 | NM_181501 | ITGA1 | Integrin, alpha 1 |
| D11 | NM_002203 | ITGA2 | Integrin, alpha 2 (CD49B, alpha 2 subunit of VLA-2 receptor) |
| D12 | NM_002204 | ITGA3 | Integrin, alpha 3 (antigen CD49C, alpha 3 subunit of VLA-3 receptor) |
| E01 | NM_000885 | ITGA4 | Integrin, alpha 4 (antigen CD49D, alpha 4 subunit of VLA-4 receptor) |
| E02 | NM_002205 | ITGA5 | Integrin, alpha 5 (fibronectin receptor, alpha polypeptide) |
| E03 | NM_000210 | ITGA6 | Integrin, alpha 6 |
| E04 | NM_002210 | ITGAV | Integrin, alpha V (vitronectin receptor, alpha polypeptide, antigen CD51) |
| E05 | NM_002211 | ITGB1 | Integrin, beta 1 (fibronectin receptor, beta polypeptide, antigen CD29 includes MDF2, MSK12) |
| E06 | NM_000212 | ITGB3 | Integrin, beta 3 (platelet glycoprotein IIIa, antigen CD61) |
| E07 | NM_002213 | ITGB5 | Integrin, beta 5 |
| E08 | NM_000888 | ITGB6 | Integrin, beta 6 |
| E09 | NM_002745 | MAPK1 | Mitogen-activated protein kinase 1 |
| E10 | NM_002746 | MAPK3 | Mitogen-activated protein kinase 3 |
| E11 | NM_002415 | MIF | Macrophage migration inhibitory factor (glycosylation-inhibiting factor) |
| E12 | NM_002421 | MMP1 | Matrix metallopeptidase 1 (interstitial collagenase) |
| F01 | NM_004530 | MMP2 | Matrix metallopeptidase 2 (gelatinase A, 72 kDa gelatinase, 72 kDa type IV collagenase) |
| F02 | NM_002423 | MMP7 | Matrix metallopeptidase 7 (matrilysin, uterine) |
| F03 | NM_004994 | MMP9 | Matrix metallopeptidase 9 (gelatinase B, 92 kDa gelatinase, 92 kDa type IV collagenase) |
| F04 | NM_002607 | PDGFA | Platelet-derived growth factor alpha polypeptide |
| F05 | NM_000930 | PLAT | Plasminogen activator, tissue |
| F06 | NM_002658 | PLAU | Plasminogen activator, urokinase |
| F07 | NM_002659 | PLAUR | Plasminogen activator, urokinase receptor |
| F08 | NM_000301 | PLG | Plasminogen |
| F09 | NM_000314 | PTEN | Phosphatase and tensin homolog |
| F10 | NM_000963 | PTGS2 | Prostaglandin-endoperoxide synthase 2 (prostaglandin G/H synthase and cyclooxygenase) |
| F11 | NM_006908 | RAC1 | Ras-related C3 botulinum toxin substrate 1 (rho family, small GTP binding protein Rac1) |
| F12 | NM_001664 | RHOA | Ras homolog gene family, member A |
| G01 | NM_000602 | SERPINE1 | Serpin peptidase inhibitor, clade E (nexin, plasminogen activator inhibitor type 1), member 1 |
| G02 | NM_003150 | STAT3 | Signal transducer and activator of transcription 3 (acute-phase response factor) |
| G03 | NM_003186 | TAGLN | Transgelin |
| G04 | NM_003236 | TGFA | Transforming growth factor, alpha |
| G05 | NM_000660 | TGFB1 | Transforming growth factor, beta 1 |
| G06 | NM_003243 | TGFBR3 | Transforming growth factor, beta receptor III |
| G07 | NM_003254 | TIMP1 | TIMP metallopeptidase inhibitor 1 |
| G08 | NM_000594 | TNF | Tumor necrosis factor |
| G09 | NM_003376 | VEGFA | Vascular endothelial growth factor A |
| G10 | NM_000638 | VTN | Vitronectin |
| G11 | NM_003882 | WISP1 | WNT1 inducible signaling pathway protein 1 |
| G12 | NM_003392 | WNT5A | Wingless-type MMTV integration site family, member 5A |

Example 3a

Figure 3:
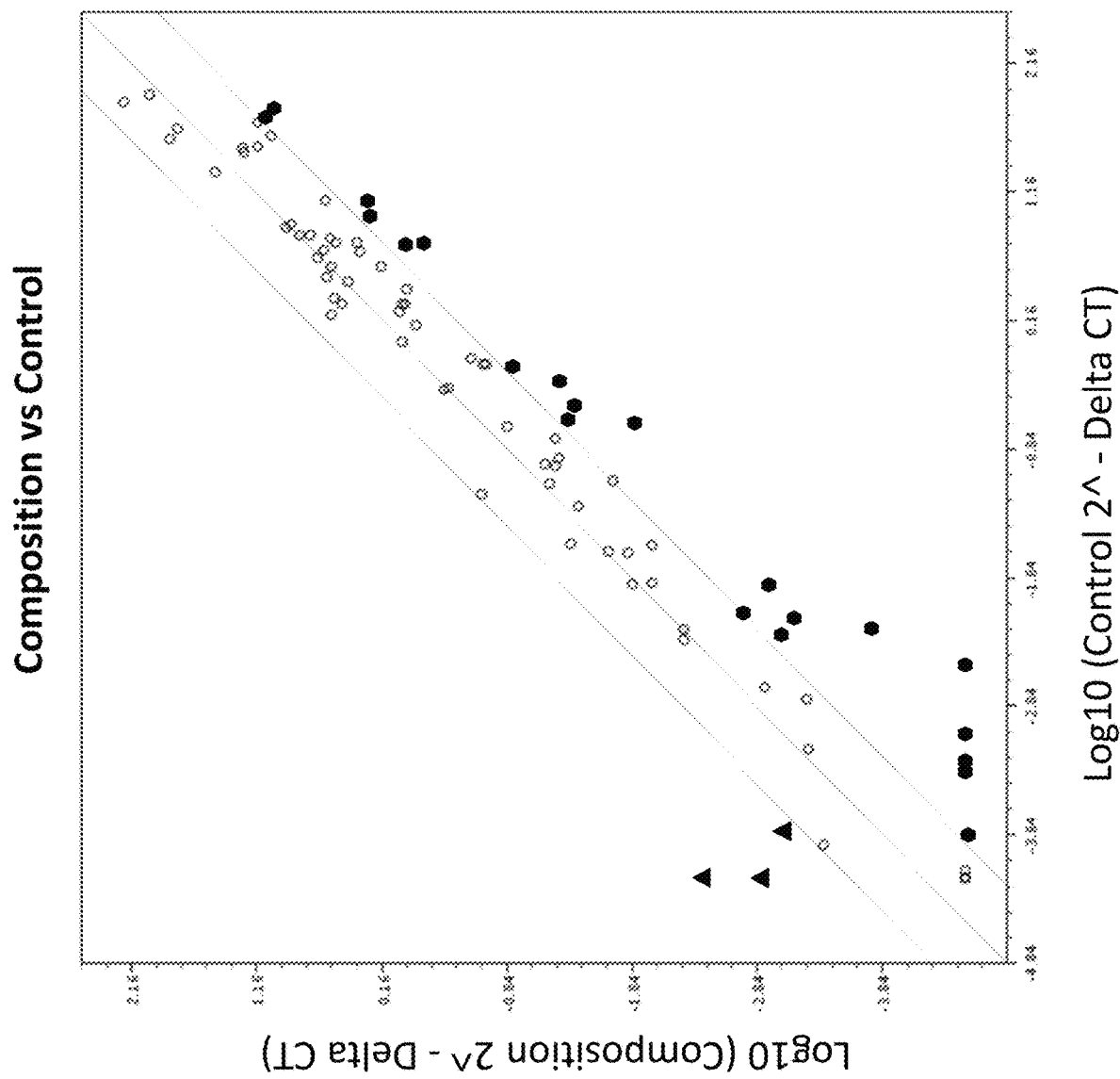
FIG. 3 shows RT2 qPCR of fibroblast monoculture comparing cells exposed to the composition versus a control (untreated cells).

In fibroblast monoculture, 2 genes were found to be upregulated and 22 were downregulated when treated with the composition versus the control (untreated cells). Results are shown in FIG. 3a and Table 8 below.

| Position | Gene | Fold Regulation |
|---|---|---|
| Up-Regulated Genes | | |
| B01 | COL4A3 | 19.2929 |
| F08 | PLG | 5.579 |
| Down-Regulated Genes | | |
| A02 | ACTC1 | −11.0809 |
| A06 | CD40LG | −14.8254 |
| B10 | CTSK | −4.2871 |
| B11 | CTSV | −9.5798 |
| C01 | CXCL11 | −4.5948 |
| C04 | EGF | −33.8246 |
| C06 | F13A1 | −92.4115 |
| C07 | F3 | −7.3107 |
| C09 | FGF10 | −27.4741 |
| D05 | IL1B | −4.084 |
| D07 | IL4 | −15.8895 |
| D10 | ITGA1 | −5.0281 |
| E05 | ITGB1 | −6.2767 |
| E07 | ITGB5 | −4.8906 |
| E08 | ITGB6 | −16.4498 |
| F09 | PTEN | −8.5742 |
| F11 | RAC1 | −8.6939 |
| F12 | RHOA | −6.021 |
| G02 | STAT3 | −4.5948 |
| G10 | VTN | −5.8159 |
| G12 | WNT5A | −16.2234 |

Example 3b

Figure 4:
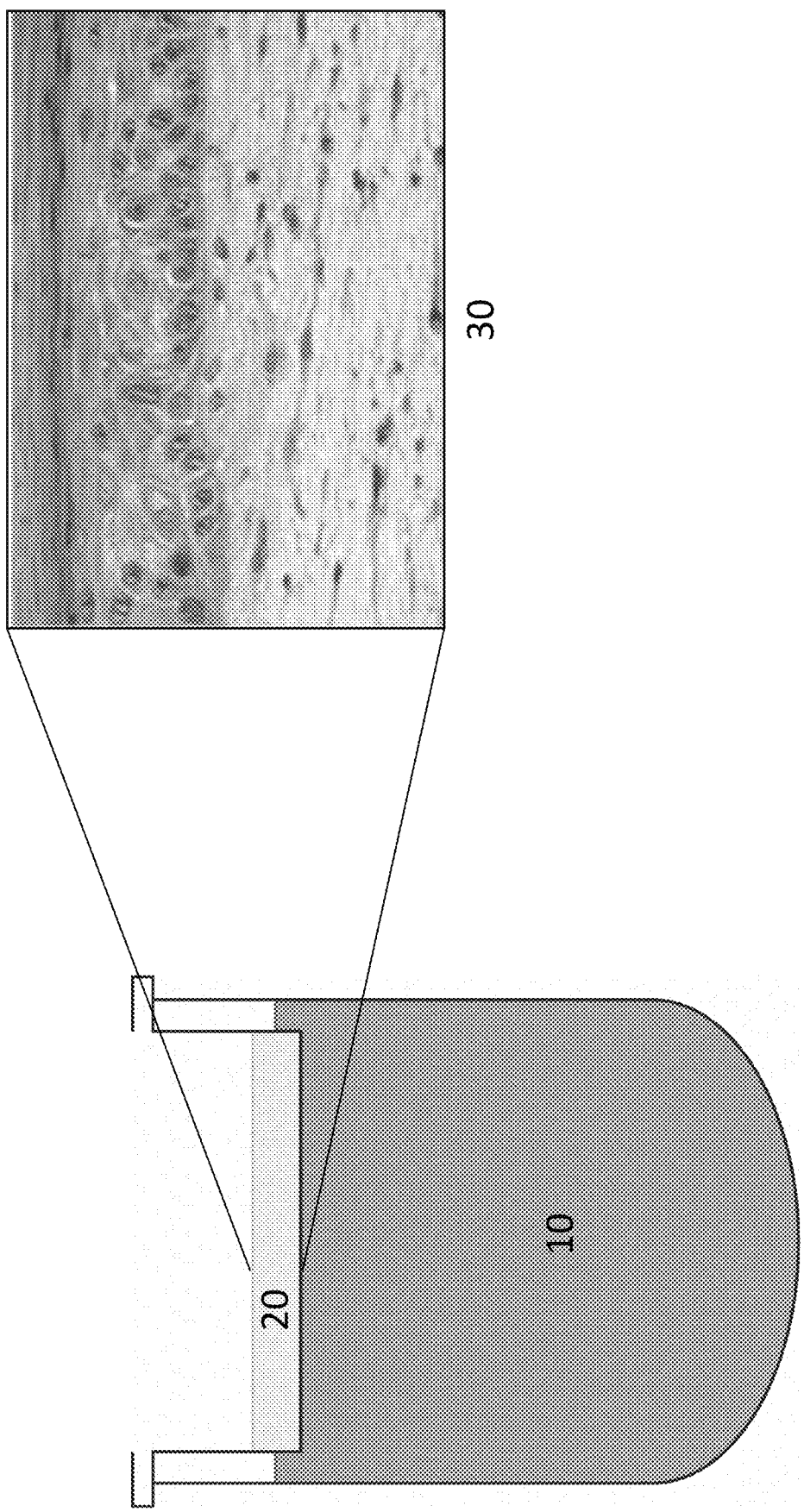
FIG. 4 shows a representation of the LabSkin system including a cross section through the striated skin. Well insert contains cultured cells in 3D fibrin scaffold.

Development of In Vitro Human 3D Deep-Skin Technology & Application in Burn Research A highly advanced 3D living skin equivalent model (developed by Dr Ronan Murphy's team at Dublin City University) is unique in providing unrivalled opportunities for non-animal testing and research. The fully differentiated epidermis is supported by a dermal component consisting of fibroblasts in a fibrin matrix. The model also allows microorganisms to be grown on its surface, mimicking infection or the skin's natural microflora. This configuration ensures we can assess topical formulations with possibly the most comprehensive range of tests available in an in vitro model. A schematic of the system is shown in FIG. 4. Culture medium 10 sits below the skin 20 to provide nutrients for growth. The resulting skin is stratified as shown in the cross section 30.

Skin Model Burn Protocol

Figure 5B:
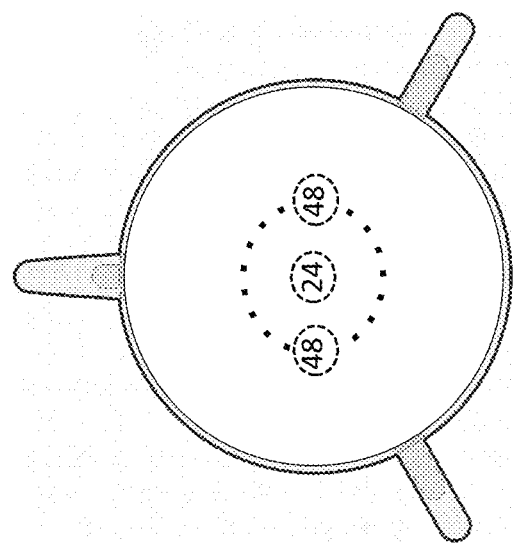
FIG. 5a shows the brass weights that we employed in inflicting thermal burn injury and FIG. 5b shows the location of subsequent skin biopsies following burn injury.
Figure 5A:
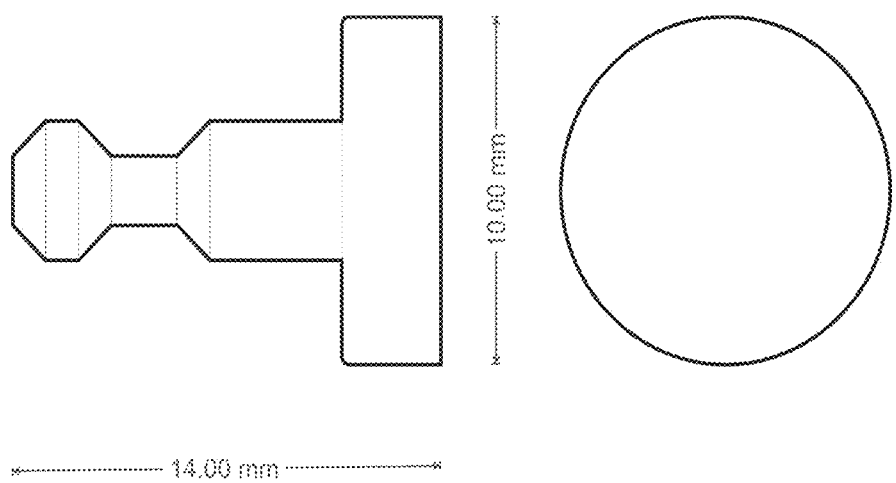
Figure 5A:
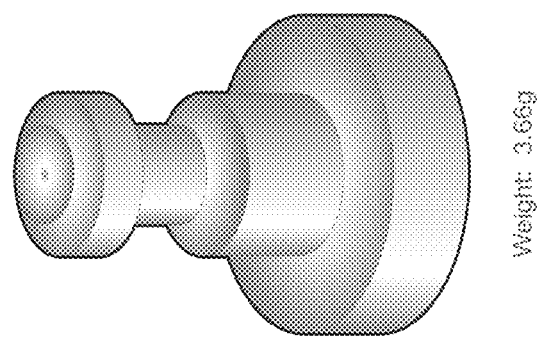

Custom 3.66 g brass weights were milled from brass stock with a surface contact area of 10 mm and a protrusion for handling with tweezers (see FIG. 5a). The weights were heated to 100° C. on a heating block (Stuart) and temperature checked using an IR thermometer.

Skin models were removed from the 6-well plate and placed onto a plastic surface in a laminar hood to avoid heat dissipation. Brass weights were removed from the heating block using tweezers and immediately placed on the centre of each 2.5 cm model for 10 seconds. After 10 seconds, the brass weight was removed and the appropriate treatment was applied.

Each treatment consisted of custom cut 2.5 cm gauze disks (Water-jel) soaked in different formulations.

Figure 6B:
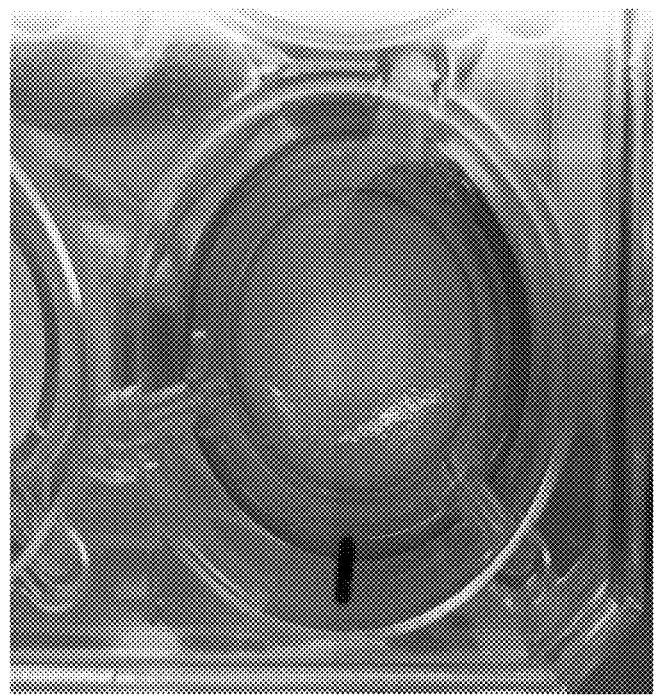
FIGS. 6a and 6b show six samples (numbered 1-6) of the damaged (burned) skin 24 hours after burns were inflicted.
Figure 6A:

Model skin turned white in the centre following removal of the weight. FIGS. 6a and 6b show photographs of six of the models (numbered 1-6) 24 hours after the burn infliction.

All models were biopsied using a 3 mm biopsy punch (Miltex) in the centre and at the burn boundary 24 and 48 hours after the burn was inflicted (see FIG. 5b), and conditioned media was sampled.

Genes associated with wound (burn) repair are:

Extracellular Matrix & Cell Adhesion:

ECM Components: COL14A1, COL1A1, COL1A2, COL3A1, COL4A1, COL4A3, COL5A1, COL5A2, COL5A3, VTN.

Remodelling Enzymes: CTSG, CTSK, CTSL2, F13A1, F3 (Tissue Factor), FGA (Fibrinogen), MMP1, MMP2, MMP7, MMP9, PLAT (tPA), PLAU (uPA), PLAUR (uPAR), PLG, SERPINE1 (PAI-1), TIMP1.

Cellular Adhesion: CDH1 (E-cadherin), ITGA1, ITGA2, ITGA3, ITGA4, ITGA5, ITGA6, ITGAV, ITGB1, ITGB3, ITGB5, ITGB6.

Cytoskeleton: ACTA2 (a-SMA), ACTC1, RAC1, RHOA, TAGLN.

Inflammatory Cytokines & Chemokines:

CCL2 (MCP-1), CCL7 (MCP-3), CD40LG (TNFSF5), CXCL1, CXCL11 (ITAC/IP-9), CXCL2, CXCL5 (ENA-78/LIX), IFNG, IL10, IL1B, IL2, IL4, IL6.

Growth Factors:

ANGPT1, CSF2 (GM-CSF), CSF3 (GCSF), CTGF, EGF, FGF10, FGF2, FGF7, HBEGF (DTR),

HGF, IGF1, MIF, PDGFA, TGFA, TGFB1, TNF, VEGFA

Signal Transduction:

TGFß: TGFB1, TGFBR3, STAT3.

WNT: CTNNB1, WISP1, WNT5A.

Phosphorylation: MAPK1 (ERK2), MAPK3 (ERK1), PTEN.

Receptors: EGFR, IL6ST (GP130).

Other: PTGS2.

Figure 8A:
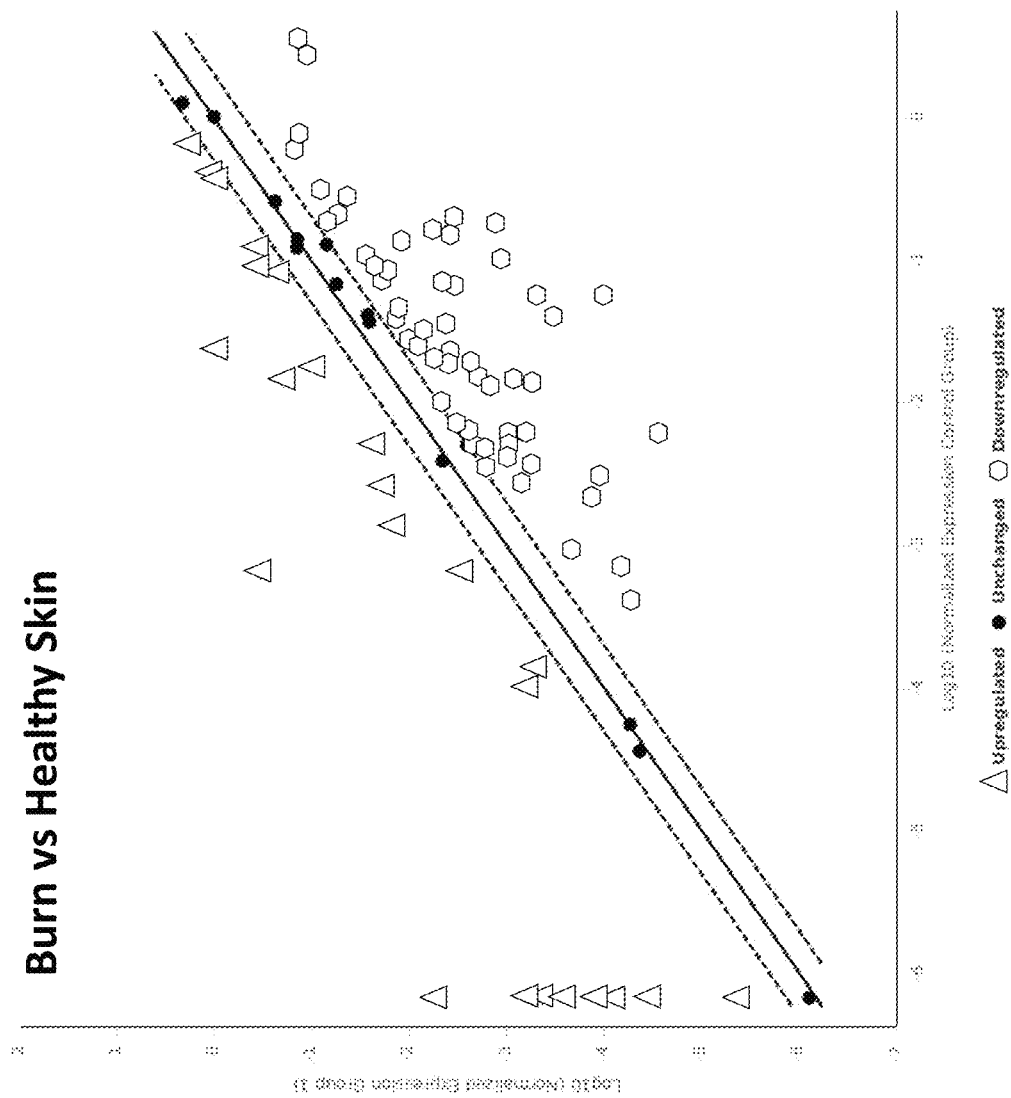
FIG. 8a shows wound healing PCR arrays revealing up- and down-regulated genes in 3D skin models in response to thermal burn injury (no treatment) vs healthy skin. Total RNA from 3D skin models were characterised, and the relative expression levels for each gene in the two samples (burn vs healthy skin) are plotted against each other in the Scatter Plot.

Firstly, RT2 qPCR was first employed to compared burned skin to healthy skin to obtain a baseline. FIG. 8a shows up- and down-regulated genes in 3D skin models in response to thermal burn injury (no treatment) vs healthy skin. Total RNA from 3D skin models was characterised, and the relative expression levels for each gene in the two samples (burn vs healthy skin) plotted against each other in the Scatter Plot. Table 10 shows 22 genes that are upregulated in burned skin relative to unburned skin. Table 11 shows 49 genes that are down regulated in thermally injured (burned) skin relative to unburned skin.

TABLE 10

| Position | Gene | Fold Change |
| --- | --- | --- |
| C03 | CXCL5 | 6942.47 |
| E06 | ITGB3 | 785.57 |
| C06 | F13A1 | 620.97 |
| B05 | CSF2 | 503.94 |
| G08 | TNF | 156.36 |
| D06 | IL2 | 112.45 |
| C08 | FGA | 105.14 |
| C01 | CXCL11 | 45.2 |
| D08 | IL6 | 36.04 |
| F10 | PTGS2 | 12.85 |
| A04 | CCL2 | 9.69 |
| C02 | CXCL2 | 6.45 |
| D02 | IFNG | 5.78 |
| A06 | CD40LG | 5.59 |
| F02 | MMP7 | 4.78 |
| B06 | CSF3 | 4.2 |
| D05 | IL1B | 4.1 |
| G07 | TIMP1 | 3.79 |
| D07 | IL4 | 3.32 |
| G01 | SERPINE1 | 2.77 |
| B12 | CXCL1 | 2.65 |
| F01 | MMP2 | 2.4 |

TABLE 11

| Position | Gene | Fold Change |
| --- | --- | --- |
| A07 | CDH1 | −565.25 |
| E08 | ITGB6 | −239.99 |
| E03 | ITGA6 | −144.31 |
| C12 | HBEGF | −122.9 |
| B11 | CTSV | −118.6 |
| D12 | ITGA3 | −91.25 |
| F06 | PLAU | −30.44 |
| D03 | IGF1 | −27.01 |
| F04 | PDGFA | −24.48 |
| D11 | ITGA2 | −19.13 |
| D04 | IL10 | −17.43 |
| F11 | RAC1 | −16 |
| B09 | CTSG | −15.86 |
| G04 | TGFA | −11.3 |
| G10 | VTN | −10.43 |
| B08 | CTNNB1 | −8.7 |
| F09 | PTEN | −8.28 |
| B04 | COL5A3 | −8.16 |
| G02 | STAT3 | −8.12 |
| A02 | ACTC1 | −7.78 |
| E04 | ITGAV | −7.62 |
| B01 | COL4A3 | −6.28 |
| A12 | COL4A1 | −5.87 |
| C07 | F3 | −5.42 |
| A09 | COL1A1 | −5.37 |
| E01 | ITGA4 | −5.22 |
| G03 | TAGLN | −5.02 |
| F12 | RHOA | −4.91 |
| A03 | ANGPT1 | −4.56 |
| A11 | COL3A1 | −4.43 |
| A08 | COL14A1 | −4.25 |
| G06 | TGFBR3 | −4.17 |
| F08 | PLG | −4.06 |
| E07 | ITGB5 | −3.96 |
| E09 | MAPK1 | −3.95 |
| A10 | COL1A2 | −3.81 |
| B03 | COL5A2 | −3.79 |
| F03 | MMP9 | −3.77 |
| E02 | ITGA5 | −3.76 |

TABLE 11-continued

| Position | Gene | Fold Change |
|---|---|---|
| B02 | COL5A1 | -3.43 |
| E10 | MAPK3 | -3.37 |
| C10 | FGF2 | -3.26 |
| A01 | ACTA2 | -2.89 |
| C05 | EGFR | -2.83 |
| D10 | ITGA1 | -2.8 |
| D01 | HGF | -2.44 |
| A05 | CCL7 | -2.3 |
| G11 | WISP1 | -2.21 |
| B07 | CTGF | -2.18 |

Next, wound healing PCR arrays revealed up- and down-regulated genes in 3D skin models in response to treatment with NB105-146 for thermal burn injury.

Figure 8B:
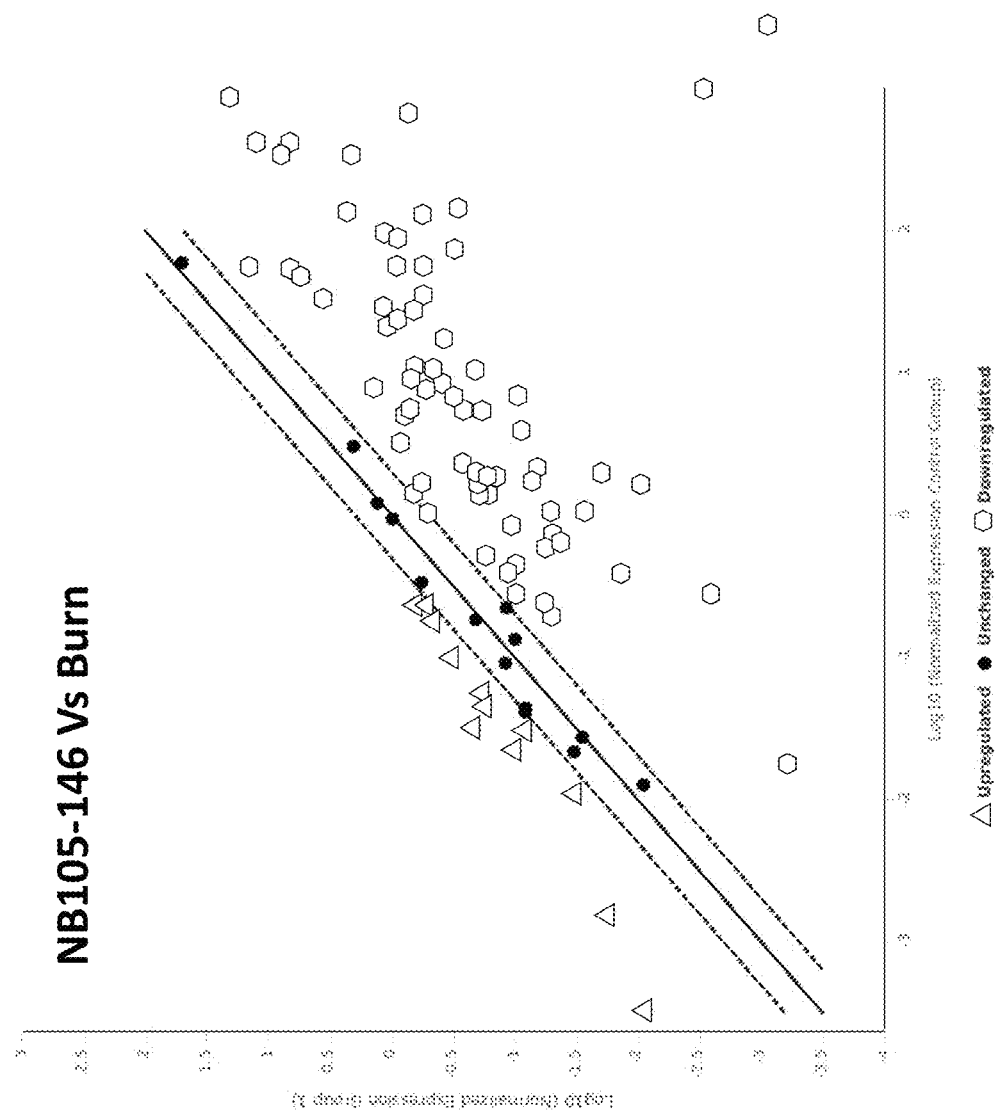
FIG. 8b shows wound healing PCR arrays revealing up- and down-regulated genes in 3D skin models in response to treatment with NB105-146 (gel formulation without mineral complex) for thermal burn injury. Total RNA from 3D skin models were characterised, and the relative expression levels for each gene in the two samples (treated vs burn (untreated) skin) are plotted against each other in the Scatter Plot.

Total RNA from 3D skin models were characterised, and the relative expression levels for each gene in the two samples (burn (untreated) vs burned and treated with gel without mineral complex) are plotted against each other in the Scatter Plot. Results are shown in FIG. 8b and Tables 12 and 13.

Table 12 shows 12 genes that are up-regulated in response to treatment with NB105-146 relative to thermal burn injured (untreated) skin. Table 13 shows 57 genes that are down-regulated in response to NB105-146 treated versus untreated thermal burn injured skin.

TABLE 12

| Position | Gene | Fold Change |
|---|---|---|
| C09 | FGF10 | 26.19 |
| A06 | CD40LG | 10.89 |
| D06 | IL2 | 6.65 |
| C04 | EGF | 4.43 |
| D03 | IGF1 | 3.62 |
| H06 | HGDC | 3.35 |
| B09 | CTSG | 3.16 |
| E08 | ITGB6 | 2.95 |
| C08 | FGA | 2.78 |
| D02 | IFNG | 2.63 |
| C06 | F13A1 | 2.61 |
| B01 | COL4A3 | 2.2 |

TABLE 13

| Position | Gene | Fold Change |
|---|---|---|
| G01 | SERPINE1 | -499.23 |
| F10 | PTGS2 | -246.35 |
| B05 | CSF2 | -238.7 |
| C07 | F3 | -180.08 |
| D08 | IL6 | -169.09 |
| B08 | CTNNB1 | -110.64 |
| E12 | MMP1 | -106.16 |
| B12 | CXCL1 | -102.5 |
| C03 | CXCL5 | -99.01 |
| G09 | VEGFA | -83.69 |
| C02 | CXCL2 | -76.57 |
| F07 | PLAUR | -64.15 |
| F02 | MMP7 | -64.13 |
| G07 | TIMP1 | -61.21 |
| E05 | ITGB1 | -50.11 |
| F01 | MMP2 | -50.02 |
| H01 | ACTB | -47.39 |
| A01 | ACTA2 | -45.62 |
| E11 | MIF | -40.95 |
| D05 | IL1B | -39.86 |
| C05 | EGFR | -39.4 |
| H05 | RPLP0 | -33.51 |
| E07 | ITGB5 | -32.45 |
| B02 | COL5A1 | -29.47 |

TABLE 13-continued

| Position | Gene | Fold Change |
|---|---|---|
| A12 | COL4A1 | -28.78 |
| F05 | PLAT | -28.73 |
| E10 | MAPK3 | -26.37 |
| G05 | TGFB1 | -25.26 |
| D09 | IL6ST | -24.61 |
| G02 | STAT3 | -24.3 |
| E09 | MAPK1 | -23.23 |
| G12 | WNT5A | -21.34 |
| B10 | CTSK | -21.29 |
| F12 | RHOA | -21.12 |
| A04 | CCL2 | -20.78 |
| F03 | MMP9 | -17.38 |
| G11 | WISP1 | -14.98 |
| D10 | ITGA1 | -14.98 |
| E02 | ITGA5 | -14.58 |
| B06 | CSF3 | -13.47 |
| C11 | FGF7 | -12.97 |
| F09 | PTEN | -11.23 |
| F11 | RAC1 | -11.19 |
| B07 | CTGF | -9.55 |
| A10 | COL1A2 | -9.38 |
| G03 | TAGLN | -8.99 |
| F06 | PLAU | -8.37 |
| E04 | ITGAV | -8.13 |
| H09 | RTC | -7.88 |
| G04 | TGFA | -6.52 |
| B03 | COL5A2 | -5.72 |
| D12 | ITGA3 | -4.66 |
| F04 | PDGFA | -4.24 |
| B11 | CTSV | -3.99 |
| A09 | COL1A1 | -3.94 |
| C10 | FGF2 | -3.67 |
| A03 | ANGPT1 | -3.66 |

Figure 8C:
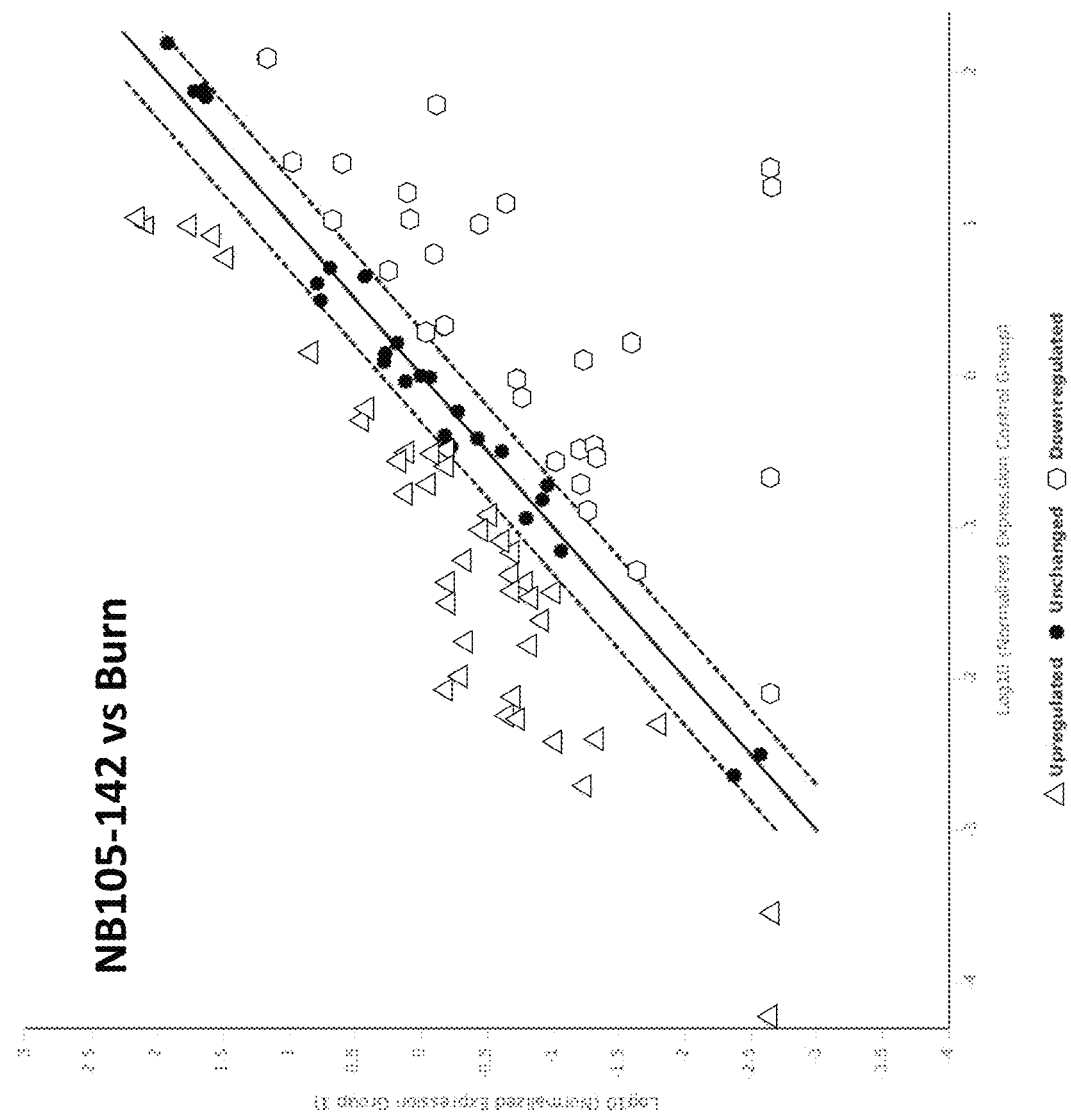
FIG. 8c shows wound healing PCR arrays revealing up- and down-regulated genes in 3D skin models in response to treatment with NB105-142 (gel formulation with mineral complex) for thermal burn injuries. Total RNA from 3D skin models were characterised, and the relative expression levels for each gene in the two samples (treated vs Burn (untreated) skin) are plotted against each other in the Scatter Plot.

Finally, wound healing PCR arrays revealed up- and down-regulated genes in 3D skin models in response to treatment with NB105-142 for thermal burn injuries. Total RNA from 3D skin models was characterised, and the relative expression levels for each gene in the two samples (WJ+Oriel vs Burn) were plotted against each other in the Scatter Plot. results are shown in FIG. 8c and Tables 14 and 15.

Table 14 shows 38 genes that are up-regulated in response to treatment with NB105-146 relative to thermal burn injured (untreated) skin. Table 15 shows 26 genes that are down-regulated in response to NB105-146 treated versus untreated thermal burn injured skin.

TABLE 14

| Position | Gene | Fold Change |
|---|---|---|
| D03 | IGF1 | 75.98 |
| B09 | CTSG | 50.93 |
| D06 | IL2 | 40.07 |
| C09 | FGF10 | 38.70 |
| C08 | FGA | 33.71 |
| E08 | ITGB6 | 29.08 |
| A07 | CDH1 | 26.53 |
| C04 | EGF | 23.98 |
| C06 | F13A1 | 19.38 |
| B01 | COL4A3 | 15.06 |
| D02 | IFNG | 14.21 |
| A11 | COL3A1 | 12.14 |
| A02 | ACTC1 | 12.00 |
| A09 | COL1A1 | 11.47 |
| F08 | PLG | 8.99 |
| A06 | CD40LG | 7.86 |
| B04 | COL5A3 | 7.62 |
| D04 | IL10 | 7.59 |
| H09 | RTC | 5.53 |
| C12 | HBEGF | 5.12 |
| E06 | ITGB3 | 5.03 |

TABLE 14-continued

| Position | Gene | Fold Change |
|---|---|---|
| B03 | COL5A2 | 4.97 |
| A10 | COL1A2 | 4.71 |
| G06 | TGFBR3 | 4.67 |
| D01 | HGF | 4.52 |
| H08 | RTC | 4.48 |
| D07 | IL4 | 4.44 |
| A08 | COL14A1 | 4.19 |
| F04 | PDGFA | 4.00 |
| E03 | ITGA6 | 3.65 |
| G10 | VTN | 3.16 |
| D12 | ITGA3 | 3.02 |
| A03 | ANGPT1 | 2.97 |
| B11 | CTSV | 2.73 |
| E01 | ITGA4 | 2.69 |
| G11 | WISP1 | 2.62 |
| D11 | ITGA2 | 2.50 |
| G03 | TAGLN | 2.00 |

TABLE 15

| Position | Gene | Fold Change |
|---|---|---|
| B05 | CSF2 | −10845.5 |
| G09 | VEGFA | −7722.46 |
| A05 | CCL7 | −98.27 |
| D08 | IL6 | −83.67 |
| B06 | CSF3 | −64.95 |
| F10 | PTGS2 | −60.18 |
| C02 | CXCL2 | −21.04 |
| B12 | CXCL1 | −12.87 |
| E12 | MMP1 | −8.49 |
| F02 | MMP7 | −8.01 |
| C03 | CXCL5 | −7.12 |
| G01 | SERPINE1 | −6.69 |
| C07 | F3 | −6.02 |
| C11 | FGF7 | −5.68 |
| A04 | CCL2 | −5.3 |
| A01 | ACTA2 | −4.24 |
| G08 | TNF | −3.56 |
| D05 | IL1B | −3.24 |
| F03 | MMP9 | −3 |
| C05 | EGFR | −2.78 |
| G07 | TIMP1 | −2.62 |
| D10 | ITGA1 | −2.29 |
| D09 | IL6ST | −2.22 |
| B08 | CTNNB1 | −2.21 |
| F07 | PLAUR | −2.14 |
| E05 | ITGB1 | −2.06 |

Example 4

Figure 7A:
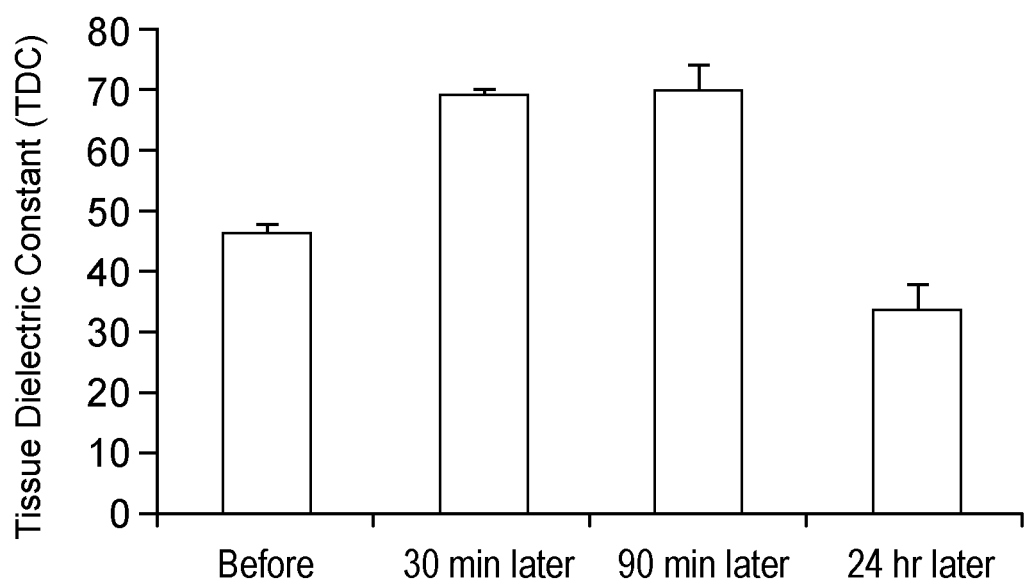
FIG. 7a shows tissue dielectric constant (TDC) as an index of localised skin water content in control model (FIG. 7a) and when treated with mineral complex (FIG. 7b).
Figure 7B:
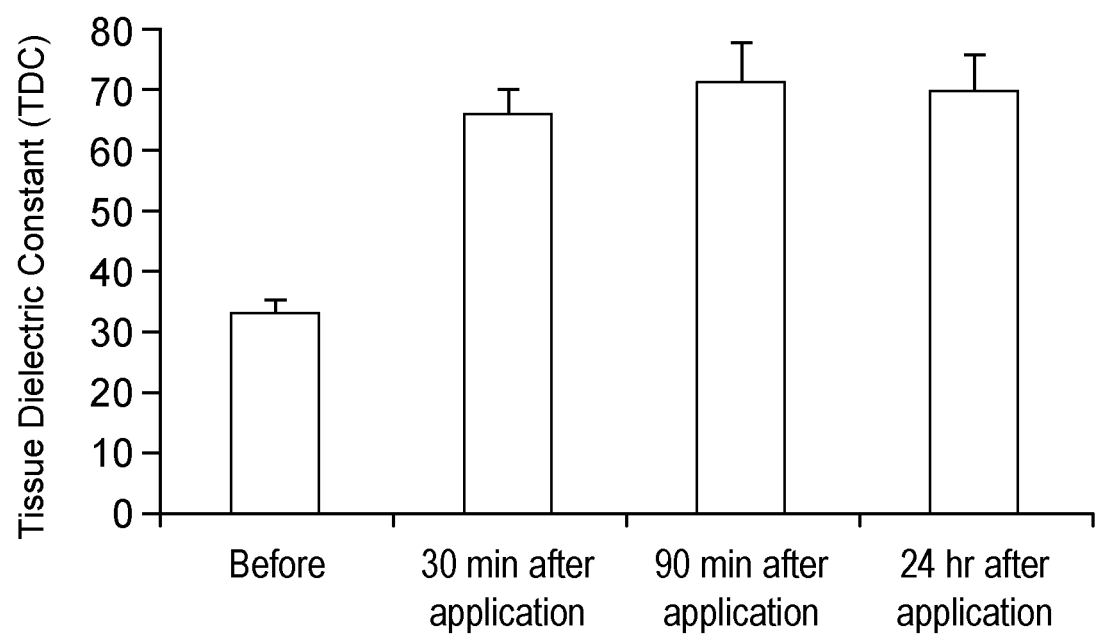

Tissue dielectric constant of burned skin models was tested at time intervals following exposure to (treatment with) the mineral complex active ingredient (FIG. 7b) versus control (treatment with nothing) (FIG. 7a).

The invention claimed is:

1. A topical composition consisting of:
   approximately 89.85% w/w purified water;
   approximately 8% w/w propanediol;
   approximately 0.8% w/w sodium acryloyldimethyltaurate/VP crosspolymer;
   approximately 1% w/w combination of phenoxyethanol, caprylyl glycol and chlorphenesin;
   approximately 0.25% w/w mineral complex; and
   approximately 0.1% w/w polyaminopropyl biguanide (PHMB) of the composition;
   wherein the composition has a viscosity approximately in the range of 200-6000 cP at 25° C. following exposure to gamma radiation.

2. A topical composition according to claim 1 wherein the mineral complex is sea water extract.

3. A topical composition according to claim 1 wherein the mineral complex comprises magnesium, potassium, sodium, boron, calcium and optionally one or more from the group consisting: copper, nickel, silicon, zinc, aluminium, arsenic, barium, cadmium, cobalt, chromium, iron, mercury, manganese, lead, antimony, selenium, tin, strontium, titanium and vanadium.

4. A topical composition according to claim 1 wherein the composition has a specific gravity of approximately 1.000±0.05 at 25° C.

5. A topical composition according to claim 1 wherein the composition has a pH approximately in the range 4.0-6.5 at 25° C.

6. A burn dressing comprising a topical composition according to claim 1 and a dressing material.

7. A burn dressing according to claim 6 wherein the dressing material comprises thermal bonded, non-woven material.

8. A burn dressing according to claim 6 wherein the dressing material comprises super absorbent material.

9. A burn dressing according to claim 6 wherein the dressing material comprises polypropylene fibre and rayon fibre.

10. A burn dressing according to claim 8 wherein the dressing material is approximately 20% super absorbent fibre.

11. A burn dressing according to claim 6 wherein the dressing material has one of more of the properties selected from the group consisting of: a weight of approximately 50 gsm, a thickness of approximately 0.63 mm, a tensile strength of approximately 4.2 N or 24.3 N, an absorbent capacity of approximately 22.7 g/g and an absorbent volume of approximately >1150 gsm.

12. A method of sterilising a topical composition according to claim 1 comprising applying gamma radiation of approximately 25.0 to 44.5 kGy to the composition.

13. A method of sterilising according to claim 12 wherein the gamma radiation is cobalt 60 irradiation.

14. A composition according to claim 1 which has been sterilised using the method of claim 12.

15. A kit of parts comprising a composition according to claim 1 and a dressing material.

16. A method of prophylaxis or treatment of a burn comprising the step of applying a topical composition according to claim 1 to skin in need thereof.

17. A method of prophylaxis or treatment according to claim 16 wherein the composition is applied for approximately 24 hours.

18. A burn dressing according to claim 6 which has been sterilised using the method of claim 12.

19. A method of prophylaxis or treatment of a burn comprising the step of applying a burn dressing according to claim 6 to skin in need thereof.

20. A method of prophylaxis or treatment according to claim 19 wherein the dressing is applied for approximately 24 hours.

* * * * *